(12) United States Patent
Ohta et al.

(10) Patent No.: US 11,648,562 B2
(45) Date of Patent: May 16, 2023

(54) ANONYMIZED DIAGNOSIS VIA LATERAL FLOW ASSAYS

(71) Applicant: International Business Machines Corporation, Armonk, NY (US)

(72) Inventors: Ricardo L. Ohta, Sao Paulo (BR); Jaione Tirapu Azpiroz, Rio de Janeiro (BR); Ademir F. Silva, Sao Paulo (BR); Matheus Esteves Ferreira, Rio de Janeiro (BR); Mathias B. Steiner, Rio de Janeiro (BR)

(73) Assignee: International Business Machines Corporation, Armonk, NY (US)

( * ) Notice: Subject to any disclaimer, the term of this patent is extended or adjusted under 35 U.S.C. 154(b) by 768 days.

(21) Appl. No.: 16/671,284

(22) Filed: Nov. 1, 2019

(65) Prior Publication Data
US 2021/0129133 A1 May 6, 2021

(51) Int. Cl.
*B01L 3/00* (2006.01)
*G16H 10/40* (2018.01)
(Continued)

(52) U.S. Cl.
CPC .............. *B01L 3/508* (2013.01); *G16H 10/40* (2018.01); *G16H 10/60* (2018.01);
(Continued)

(58) Field of Classification Search
CPC .............. B01L 3/508; B01L 2300/021; B01L 2300/0816; B01L 2300/0825;
(Continued)

(56) References Cited

U.S. PATENT DOCUMENTS

| 4,987,127 A | 1/1991 | Sirany |
| 8,446,463 B2 | 5/2013 | Fleming et al. |

(Continued)

FOREIGN PATENT DOCUMENTS

| GB | 2553512 A | 3/2018 |
| WO | 2016150134 A1 | 9/2016 |

OTHER PUBLICATIONS

Mell et al., "The NIST Definition of Cloud Computing", National Institute of Standards and Technology, NIST Special Publication 800-145, Sep. 2011, 7 pages.
(Continued)

*Primary Examiner* — Jennifer Wecker
*Assistant Examiner* — Alea N. Martin
(74) *Attorney, Agent, or Firm* — Kelsey M. Skodje

(57) ABSTRACT

Method, apparatus, and computer program product are provided for anonymized diagnosis using lateral flow assays. In some embodiments, a test card includes one or more lateral flow assay (LFA) with one or more test patterns (e.g., full line, partial line, dot), one or more dummy patterns, and one or more control patterns. To visually encode LFA results, at manufacture, one or more lines/dots containing true results of the LFA(s) each has a position mixed with other "dummy" lines/dots, in randomized position patterns selected from among a plurality of possible position patterns. An optical machine-readable representation of data (e.g., QR code) is attached to the test card and encodes test card identification information (e.g., lot number, serial number, test type) associated with the test card. In some embodiments, a passcode card having a scrapeable coating that conceals a passcode associated with the test card is removably attached to the test card.

3 Claims, 13 Drawing Sheets

(51) Int. Cl.
      *G16H 10/60* (2018.01)
      *G16H 10/65* (2018.01)
(52) U.S. Cl.
      CPC . *B01L 2300/021* (2013.01); *B01L 2300/0816* (2013.01); *G16H 10/65* (2018.01)
(58) Field of Classification Search
      CPC ....... B01L 3/5023; B01L 3/545; G16H 10/40; G16H 10/60; G16H 10/65; G16H 50/20; Y02A 90/10
      See application file for complete search history.

(56) References Cited

U.S. PATENT DOCUMENTS

| | | | |
|---|---|---|---|
| 8,698,881 | B2 | 4/2014 | Fleming et al. |
| 8,824,800 | B2 | 9/2014 | Bremnes et al. |
| 9,778,200 | B2 | 10/2017 | Tsai et al. |
| 9,903,857 | B2 | 2/2018 | Polwart et al. |
| 2006/0275920 | A1 | 12/2006 | Petrilla et al. |
| 2009/0180925 | A1 | 7/2009 | Petruno et al. |
| 2011/0032525 | A1 | 2/2011 | Kurokawa et al. |
| 2016/0025752 | A1* | 1/2016 | Santiago ............... B01L 3/5023 436/501 |
| 2018/0014148 | A1 | 1/2018 | Zin et al. |
| 2018/0196037 | A1 | 7/2018 | Polwart et al. |
| 2018/0322941 | A1* | 11/2018 | Krishnan ............... G16H 40/63 |

OTHER PUBLICATIONS

Walters et al., "Modelling the global spread of diseases: A review of current practice and capability", Epidemics, vol. 25, 2018, pp. 1-8.
Zanotto et al., "The Challenges Imposed by Dengue, Zika, and Chikungunya to Brazil", Frontiers in Immunology, vol. 9, Article 1964, Aug. 2018, pp. 1-6.
Reis et al., "An Epidemiological Network Model for Disease Outbreak Detection", PLoS Medicine, vol. 4, Issue 6, e210, Jun. 2007, pp. 1019-1031.
Chao et al., "FluTE, a Publicly Available Stochastic Influenza Epidemic Simulation Model", PLoS Computational Biology, vol. 6, Issue 1, e1000656, Jan. 2010, pp. 1-8.
Koczula et al., "Lateral flow assays", Essays in Biochemistry, vol. 60, 2016, pp. 111-120.
Unknown, "Buy Best Rapid Diagnostic Test Reader | Rapid Test Reader At Home For Sale", 2 pages, printed from <http://www.chemtronbio.com/product/kd-i-rapid-test-reader.html> on Oct. 7, 2019.
Unknown, "Mobile Assay | Mobile Diagnostic Lateral Flow Test Strip Reader", 5 pages, printed from <http://www.mobileassay.com> on Oct. 7, 2019.
Unknown, "Novarum—Point of Care Readers", 3 pages, printed from <http://www.novarumdx.com> on Oct. 7, 2019.
Unknown, "Part 1: Where Are All the Multiplexed LFI's? | DCN Diagnostics", 8 pages, printed from <https://www.dcndx.com/arent-multiplexed-lateral-flow-tests/> on Oct. 7, 2019.
Grady, Denise, "Ebola Epidemic in Congo Could Last Another Year, C.D.C. Director Warns", 3 pages, printed from <https://nyti.ms/2ubFvpz> on Oct. 7, 2019.
Unknown, "Find The Right STD Test For Your Needs & Budget", 6 pages, printed from <https://stdtestoptions.info/> on Oct. 7, 2019.
Unknown, "EMPE Diagnostics—Innovators in simple and affordable diagnostics", 6 pages, printed from <https://www.empediagnostics.com/> on Oct. 7, 2019.
Cardinal, David, "What Is Mixed Reality, and Can It Take Augmented Reality Mainstream?", 7 pages, printed from <https://www.extremetech.com/extreme/249328-mixed-reality-can-take-augmented-reality-mainstream> on Oct. 7, 2019.
O'Farrell, Brendan, "Multiplexing and Arraying in Lateral Flow Assays", 13 pages, printed from <https://www.slideshare.net/ofarreb/multiplexing-and-arraying-in-lateral-flow-assays> on Oct. 7, 2019.
Unknown, "Lateral Flow Reader Customisation from Abingdon Health", 5 pages, printed from <https://www.abingdonhealth.com/contract-services/lateral-flow-reader/> on Oct. 7, 2019.
Unknown, "Changchun Wancheng Bio-Electron Co., Ltd.—Urine (Saliva) Test Strip, . . . ", 8 pages, printed from <https://jlwancheng.en.alibaba.com/> on Oct. 7, 2019.
Unknown, "Novarum—Smartphone Diagnostic Readers—YouTube", 2 pages, printed from <https://www.youtube.com/watch?v=BtqXScHmw5A> on Oct. 7, 2019.
Unknown, "Rapid Tests Market Value to Grow $39,103 Million by 2023", 2 pages, printed from <https://www.openpr.com/news/1500829/rapid-tests-market-value-to-grow-39-103-million-by-2023.html> on Oct. 7, 2019.
Unknown, "Analysis of 2018 Healthcare Data Breaches", 6 pages, printed from <https://www.hipaajournal.com/analysis-of-healthcare-data-breaches/> on Oct. 7, 2019.
Unknown, "Lateral Flow Immunoassays—Cytodiagnostics", 2 pages, printed from <http://www.cytodiagnostics.com/store/pc/Lateral-Flow-Immunoassays-d6.htm> on Oct. 7, 2019.
Unknown, "Chembio | HIV 1/2 STAT-PAK® Assay", 2 pages, printed from <http://chembio.com/hiv-12-stat-pak-assayintl/> on Oct. 7, 2019.
Unknown, "Chembio and FIND collaborate to develop point-of-care multplex test for acute febrile illnesses in Asia Pacific—FIND", 1 page, printed from <https://www.finddx.org/newsroom/chembio-and-find-collaborate-to-develop-point-of-care-multplex-test-for-acute-febrile-illnesses-in-asia-pacific/> on Oct. 7, 2019.
Unknown, "What is Symbolics?—Symbolics DX", 3 pages, printed from <http://symbolicsdx.com/what-is-symbolics/> on Oct. 7, 2019.
Gokce et al., "High-Content Optical Codes for Protecting Rapid Diagnostic Tests from Counterfeiting", Analytical Chemistry, vol. 90, 2018, pp. 7383-7390.
Scherr et al., "An embedded barcode for "connected" malaria rapid diagnostic tests", 5 pages, printed from <https://pubs.rsc.org/en/content/articlelanding/2017/lc/c6lc01580h#!divAbstract> on Oct. 8, 2019.
Park et al., "Avatar DNA Nanohybrid System in Chip-on-a-Phone", Scientific Reports, vol. 4, Article No. 4879, 2014, pp. 1-6.
Han et al., "Lithographically Encoded Polymer Microtaggant Using High-Capacity and Error-Correctable QR Code for Anti-Counterfeiting of Drugs", 2 pages, printed from <https://onlinelibrary.wiley.com/doi/abs/10.1002/adma.201201486> on Oct. 8, 2019.
Ciftlik et al., "Programmable parylene-C bonding layer fluorescence for storing information on microfluidic chips", 4 pages, printed from <https://pubs.rsc.org/en/content/articlelanding/2013/lc/c3lc41280f/unauth#!divAbstract> on Oct. 5, 2019.
Unknown, "Lateral Flow Reagent Dispenser (ALFRD) | ClaremontBio.com", 6 pages, printed from <https://www.claremontbio.com/Lateral_Flow_Reagent_Dispenser_p/07.711.01.htm> on Oct. 8, 2019.
Unknown, "Matrix 1600 Reagent Dispensing | Kinematic Automation", 2 pages, printed from <https://kinematic.com/matrix-1600-reagent-dispensing.html> on Oct. 8, 2019.
Unknown, "BioSense Platform | NSSP | CDC", 2 pages, printed from <https://www.cdc.gov/nssp/biosense/index.html> on Oct. 8, 2019.
Unknown, "GLEAMviz.org", 1 page, printed from <http://www.gleamviz.org/> on Oct. 8, 2019.
Unknown, "GitHub—dichao/FluTE: Agent-based influenza epidemic model", 8 pages, printed from <https://github.com/dlchao/FluTE> on Oct. 8, 2019.

* cited by examiner

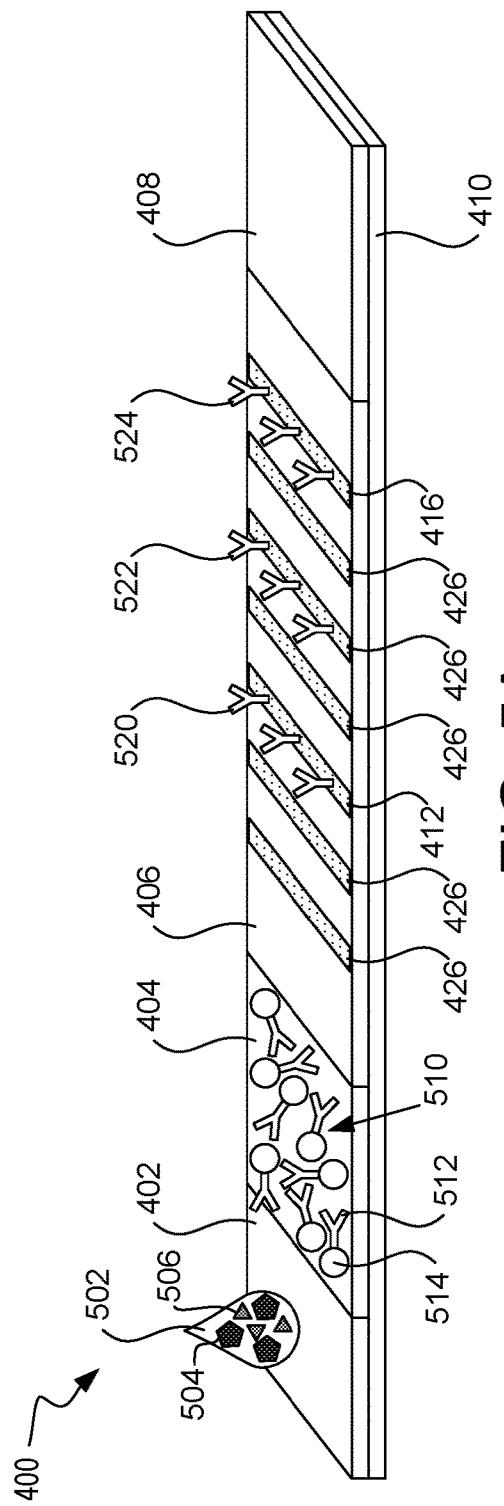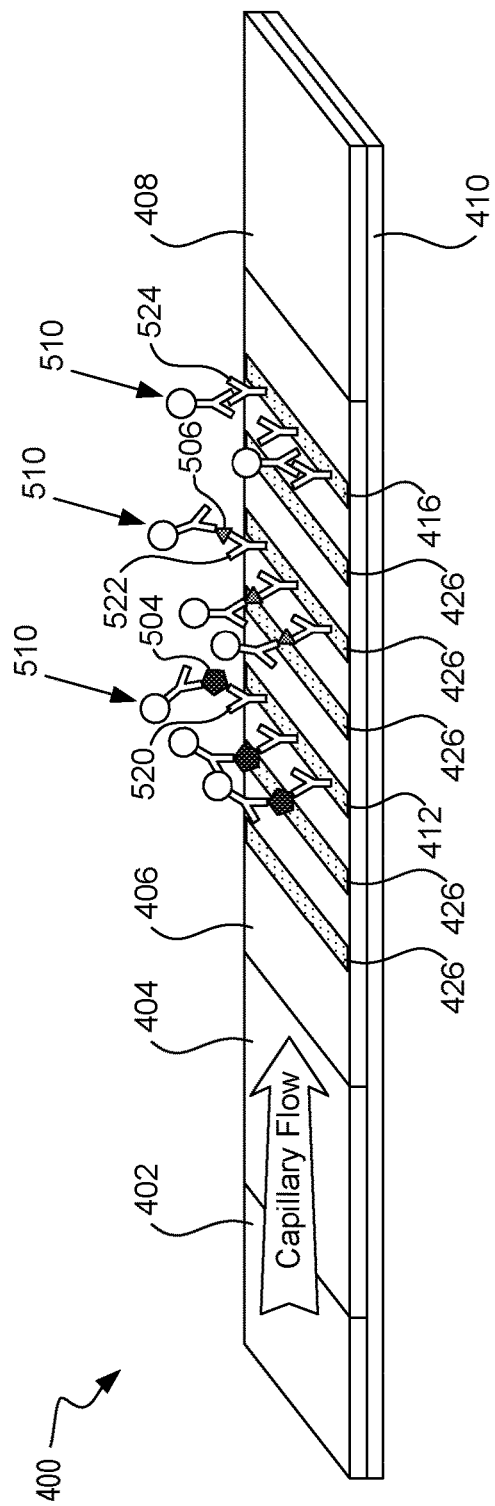

ANONYMIZED DIAGNOSIS VIA LATERAL FLOW ASSAYS

BACKGROUND

The present invention relates in general to the field of lateral flow assays. More particularly, the present invention relates to providing anonymized diagnosis using lateral flow assays.

SUMMARY

Embodiments of the present disclosure include a method, apparatus, and computer program product for providing anonymized diagnosis using lateral flow assays. In some embodiments, a lateral flow test card includes at least one lateral flow assay (LFA) with one or more test patterns (e.g., full lines, partial lines, dots, etc.), one or more dummy patterns, and one or more control patterns. To visually encode LFA results, at manufacture, one or more lines/dots containing true results of the at least one LFA each have a position mixed with other lines/dots (i.e., "dummy" lines/dots), in randomized position patterns selected from among a plurality of possible position patterns. An optical machine-readable representation of data (e.g., QR code, barcode, etc.) is attached to the test card and encodes test card identification information (e.g., lot number, serial number, test type, etc.) associated with the test card. In some embodiments, a passcode card having a concealed passcode associated with the test card is removably attached to the test card. For example, the passcode card may have a scrapeable coating that conceals the passcode until the scrapeable coating is scraped away by a user. In some embodiments, a patient barcode is attached to the test card and encodes a patient code issued to a patient at the point-of-use. The patient code includes an ID that anonymously identifies the patient, and may also include the geolocation of the point-of-use and the time of use.

BRIEF DESCRIPTION OF THE SEVERAL VIEWS OF THE DRAWINGS

Embodiments will hereinafter be described in conjunction with the appended drawings, where like designations denote like elements.

FIG. 5A illustrates an exemplary implementation of the lateral flow assay shown in FIG. 4 at initiation of test execution as a test sample is applied to a sample receiving zone of the lateral flow assay, according to one or more embodiments.

FIG. 5B illustrates an exemplary implementation of the lateral flow assay shown in FIG. 4 at completion of test execution after the test sample has flowed across the lateral flow assay to an absorbent zone, according to one or more embodiments.

DETAILED DESCRIPTION

Figure 1:
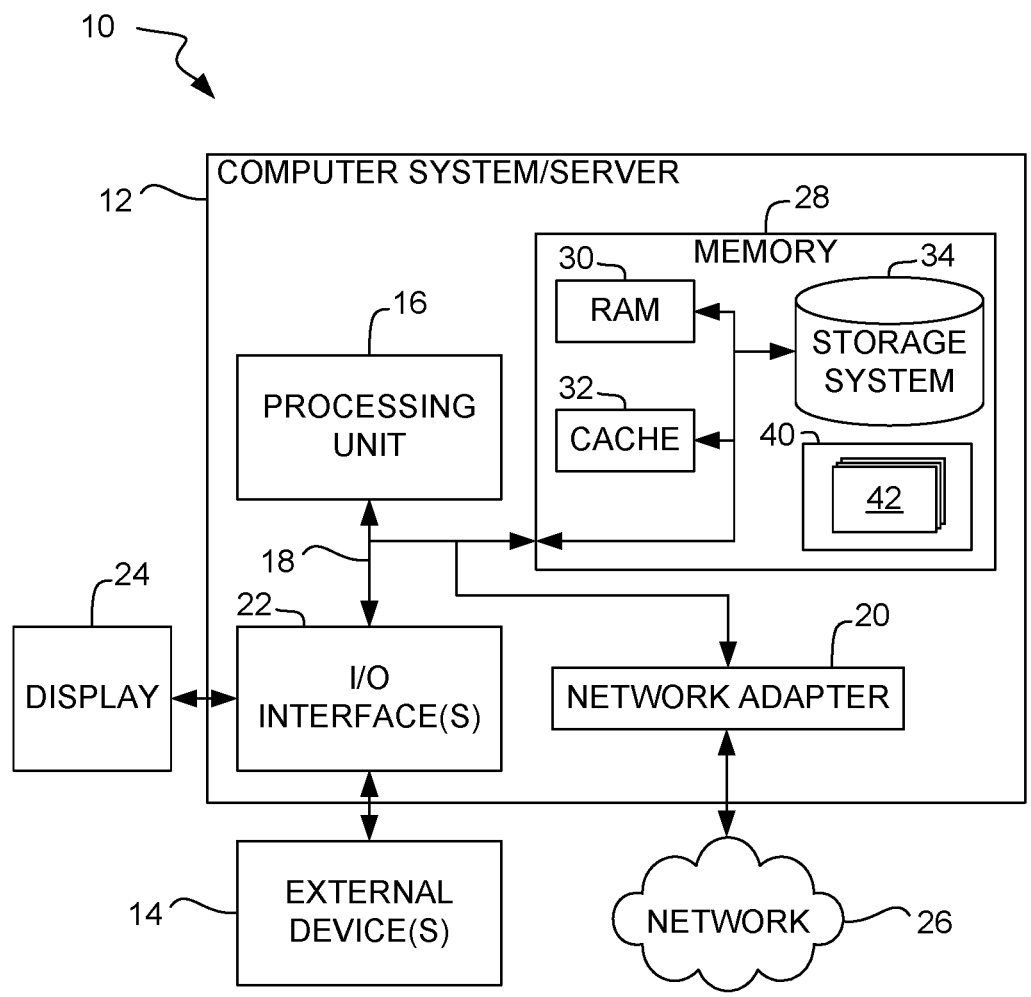
FIG. 1 depicts a cloud computing node, according to one or more embodiments.

Lateral flow assay (LFA) is a technology platform for the detection and quantification of target analytes in test samples. Typically, the LFA is a paper-based platform that is low-cost, simple to use, rapid, and portable. Portability facilitates use of the LFA at the point-of-care and/or point-of-need. Once the test sample is applied to the LFA, results are typically displayed in less than 30 minutes. These and other advantages (e.g., good sensitivity and specificity over 90%) make LFAs an ideal technology platform for providing rapid diagnosis directly to patients, as well as in physician's offices, hospitals, and clinical laboratories.

However, conventional LFA devices, also known as LFA test cards, typically provide few, if any, safeguards with respect to diagnosis confidentiality. For example, conventional LFA test cards often include the name of the disease for which the test card is designed on the test card surface, along with the written patient's name and/or patient ID. In this scenario, test results may be readily observable and understood through test result windows, raising questions of privacy and safety of sensitive medical records. In accordance with one or more embodiments, anonymized diagnosis is provided using an LFA test card enhanced to encode the test results through randomization of the location of one or more test lines, dots, or other patterns.

In accordance with one or more embodiments, a cloud-based mobile analysis system may be employed to decrypt the anonymized diagnosis using lateral flow assays.

An emerging information technology (IT) delivery model is cloud computing, by which shared resources, software, and information are provided over the Internet to computers and other devices on-demand. Cloud computing can significantly reduce IT costs and complexities while improving workload optimization and service delivery. With this approach, an application instance can be hosted and made available from Internet-based resources that are accessible through a conventional Web browser over HTTP. An example application might be one that provides a common set of messaging functions, such as email, calendaring, contact management, and instant messaging. A user would then access the service directly over the Internet. Using this service, an enterprise would place its email, calendar, and/or collaboration infrastructure in the cloud, and an end user would use an appropriate client to access his or her email, or perform a calendar operation.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, as well as removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"), and other non-removable, non-volatile media (e.g., a "solid-state drive"). Although not shown, a magnetic disk drive for reading from and writing to a removable, non-volatile magnetic disk (e.g., a "floppy disk"), and an optical disk drive for reading from and/or writing to a removable, non-volatile optical disk such as a CD-ROM, DVD-ROM or other optical media can be provided. In such instances, each can be connected to a bus 18 by one or more data media interfaces. As will be further described below, memory 28 may include a computer program product storing a set (e.g., at least one) of program modules 42 comprising computer readable instructions configured to carry out one or more features of the present invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. In some embodiments, program modules 42 are adapted to generally carry out the one or more functions and/or methodologies of one or more embodiments.

Computer system/server 12 may also communicate with one or more external devices 14 such as a keyboard, a pointing device, a display 24, etc.; one or more devices that enable a user to interact with computer system/server 12; and/or any device (e.g., network card, modem, etc.) that enable computer system/server 12 to communicate with one or more other computing devices. Such communication can occur via Input/Output (I/O) interfaces 22. Still further, computer system/server 12 can communicate with one or more networks such as a local area network (LAN), a general wide area network (WAN), and/or a public network (e.g., the Internet) via network adapter 20. As depicted, the network adapter 20 communicates with other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 2:
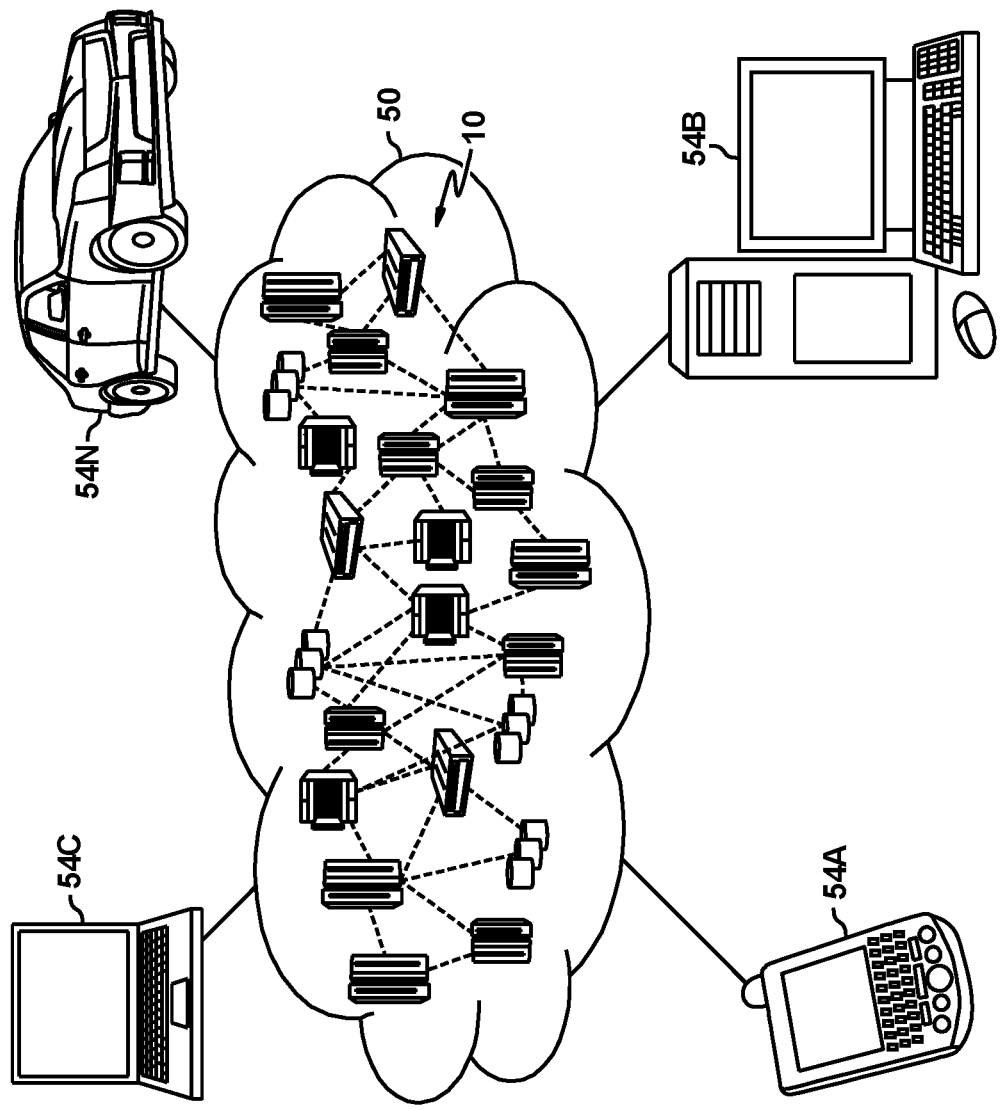
FIG. 2 depicts a cloud computing environment, according to one or more embodiments.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
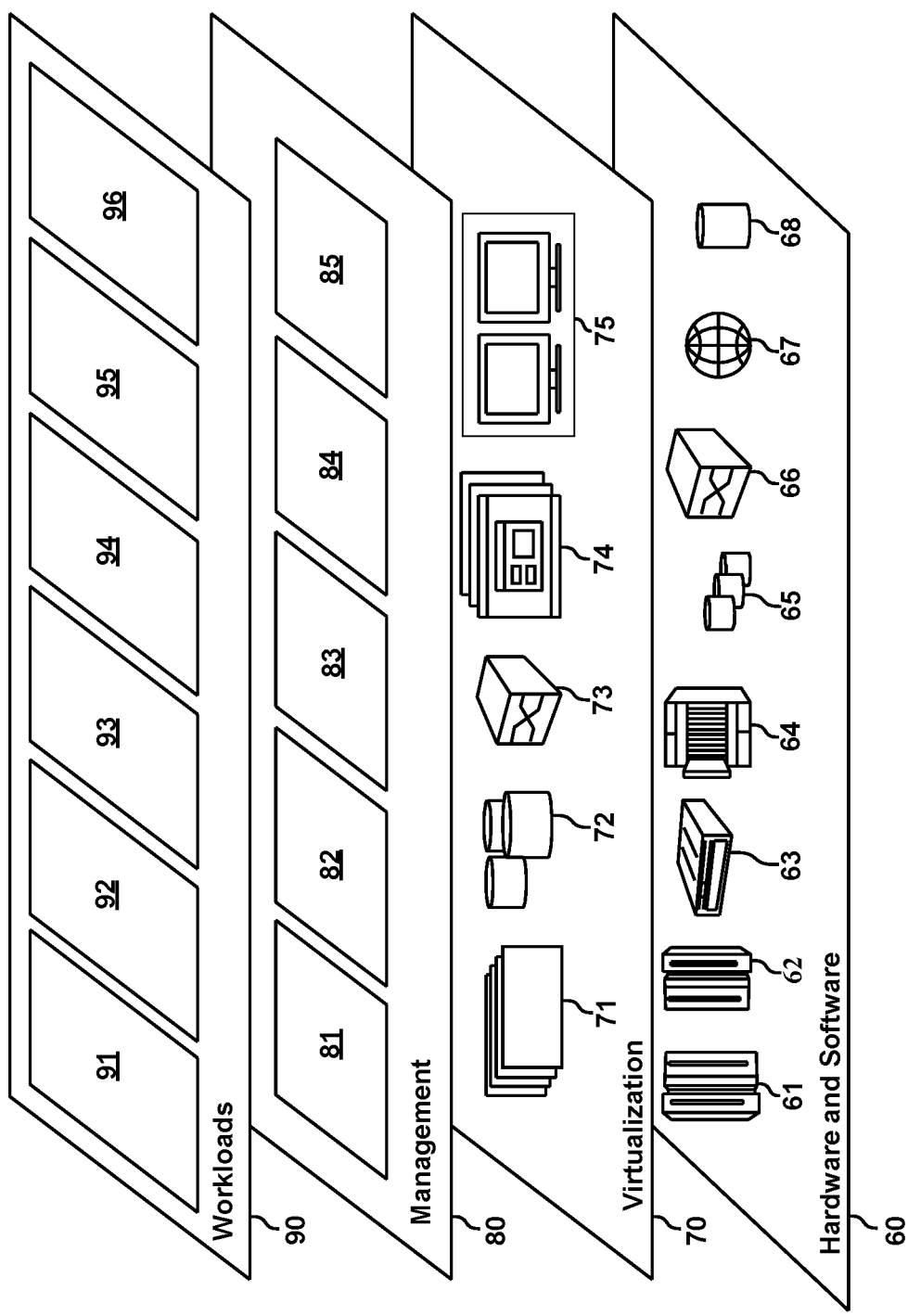
FIG. 3 depicts abstraction model layers, according to one or more embodiments.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and lateral flow assay (LFA) test analysis 96.

Lateral flow assays (LFAs) can be categorized into different types depending on the recognition elements used. The most common type of LFA is lateral flow immunoassays (LFIAs), which use antibodies as recognition elements. For example, LFIAs may be used for the detection of antibodies and other target analytes (e.g., proteins, hormones, etc.).

LFIAs are used across myriad industries. For example, LFIAs have been developed for applications in medicine, veterinary, agriculture, pharmaceutical, life sciences, food industry, feed industry, bio-defense, and environmental.

LFIAs are available for an expansive range of target analytes including, but not limited to, blood proteins, mycotoxins, viral pathogens, bacterial toxins, animal diseases, chemicals, and water pollutants.

An example of another type of LFA is nucleic acid lateral flow assays (NALFA), which use nucleic acids as recognition elements. For example, NALFAs may be used for the detection of amplicons which can be formed during the polymerase chain reaction (PRC).

Embodiments of the present disclosure include a method, apparatus, and computer program product for providing anonymized diagnosis using LFAs, which may be LFIAs, NALFAs, or any other type of LFA. In some embodiments, a lateral flow test card, also referred to herein as a "test card", includes at least one LFA with one or more test patterns (e.g., full line, partial line, dot, etc.), one or more dummy patterns, and one or more control patterns. To visually encode LFA results, at manufacture, one or more lines/dots containing true results of the at least one LFA each have a position mixed with other lines/dots (i.e., "dummy" lines/dots), in randomized position patterns selected from among a plurality of possible position patterns. An optical machine-readable representation of data (e.g., QR code, barcode, etc.) is attached to the test card and encodes test card identification information (e.g., lot number, serial number, test type, etc.) associated with the test card. In some embodiments, a passcode card having a concealed passcode associated with the test card is removably attached to the test card. For example, the passcode card may have a scrapeable coating that conceals the passcode until the scrapeable coating is scraped away by a user. In some embodiments, a patient barcode is attached to the test card and encodes a patient code issued to a patient at the point-of-use. The patient code includes an ID that anonymously identifies the patient, and may also include the geolocation of the point-of-use and the time of use.

The term "analyte" refers to a substance that can be assayed by the lateral flow assay. Examples of different types of analytes include organic compounds (e.g., proteins and amino acids), hormones, metabolites, antibodies, pathogen-derived antigen, drugs, toxins, and microorganisms (e.g., bacteria and viruses).

The term "antigen" refers to a toxin or other foreign substance which induces an immune response in the body, especially the production of antibodies.

The term "labeling substance" refers to a substance that has specific binding affinity for an analyte and that has a detectable characteristic feature that can be distinguished from other elements of the lateral flow assay. The labeling substance may include a combination of a labeling particle (e.g., a colloidal gold particle) that provides the detectable characteristic and an antibody (e.g., an immunoglobulin) that provides the specific binding affinity for the analyte. In some implementations, the labeling substances have distinctive optical properties, such as color, which allow regions of the lateral flow assay containing different labeling substances to be distinguished from one another.

The term "reagent" refers to a substance that reacts chemically or biologically with a target substance, such as a labeling substance or an analyte.

The term "capture region" refers to regions on a detection zone of a lateral flow assay that include one or more immobilized reagents. In some embodiments, a plurality of "capture regions" are arranged on a detection zone of a lateral flow assay to provide a test matrix of full lines (e.g., the full lines 614 shown in FIG. 6A, described below), partial lines on a grid (e.g., the partial lines 624 on a grid shown in FIG. 6B), partial lines not on a grid (e.g., the partial lines 634 not on a grid shown in FIG. 6C), or dots on a grid (e.g., the dots 644 on a grid shown in FIG. 6D), any of which may be a test pattern, a control pattern, or a dummy pattern.

The term "test pattern" refers to a capture region containing an immobilized reagent with a specific binding affinity for a target analyte. In some embodiments, a lateral flow assay may include one or more test patterns (e.g., full line, partial line, dot, etc.).

The term "control pattern" refers to a capture region containing an immobilized reagent with a specific binding affinity for a labeling substance for test control purposes. In some embodiments, a lateral flow assay may include one or more control patterns (e.g., full line, partial line, dot, etc.).

The term "dummy pattern" refers to a capture region containing an immobilized reagent with a specific binding affinity for a labeling substance or an analyte other than the target analyte(s) of the test pattern(s). In some embodiments, one or more dummy patterns may each be comprised of a control pattern. The dummy pattern(s) are present in the detection zone for test encoding purposes, i.e., to visually encode LFA results. In some embodiments, a lateral flow assay may include one or more dummy patterns (e.g., full line, partial line, dot, etc.).

Figure 4:
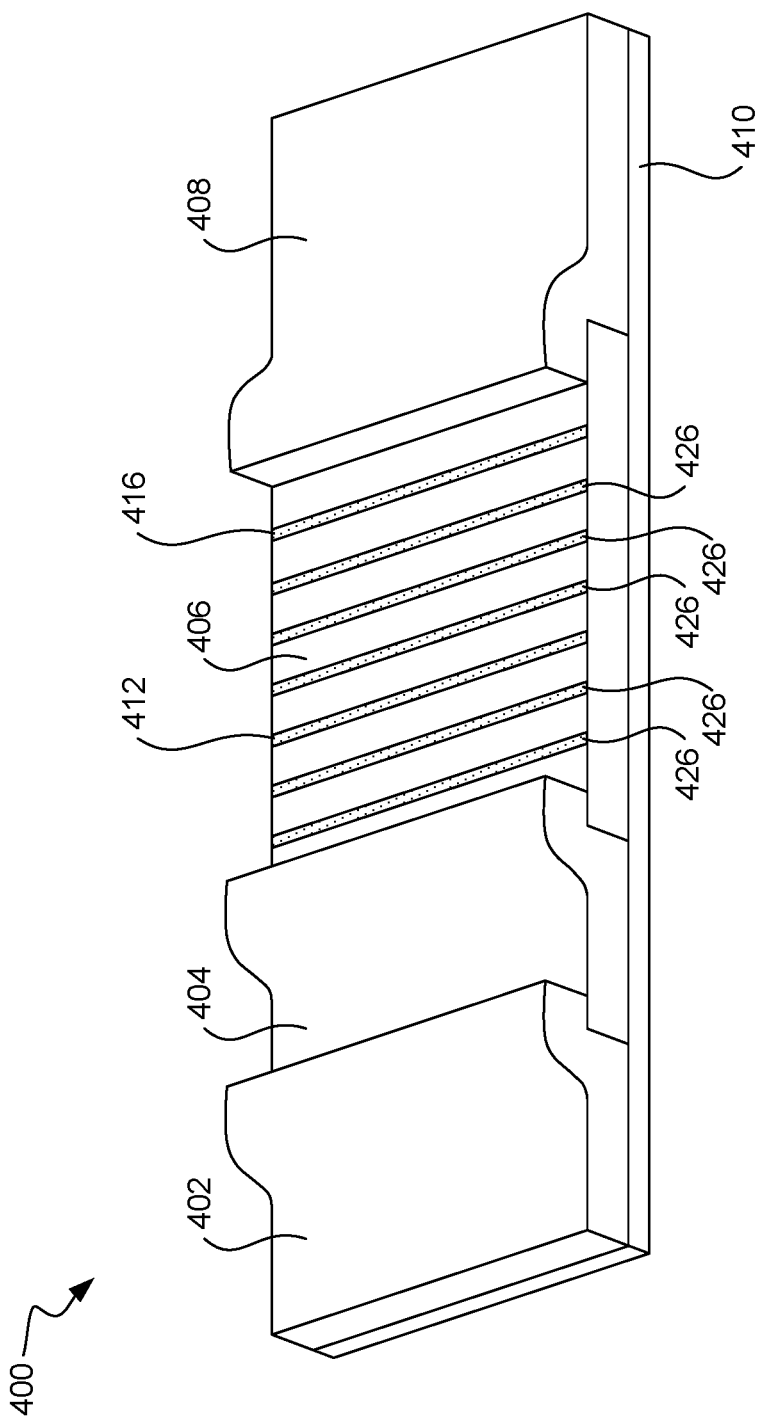
FIG. 4 depicts an exemplary lateral flow assay, according to one or more embodiments.

Referring now to FIG. 4, an exemplary lateral flow assay 400 is depicted in accordance with one or more embodiments. The exemplary lateral flow assay 400 includes a sample receiving zone 402, a labeling zone 404, a detection zone 406, and an absorbent zone 408 on a common substrate 410. As is the case with conventional lateral flow assays, the sample receiving zone 402, the labeling zone 404, the detection zone 406, and the absorbent zone 408 may be made of paper materials that allows fluid (i.e., the test sample) to flow from the sample receiving zone 402 to the absorbent zone 408 by capillary action. The materials and fabrication operations used to make conventional lateral flow assays are well known to those skilled in the art.

Figure 7A:
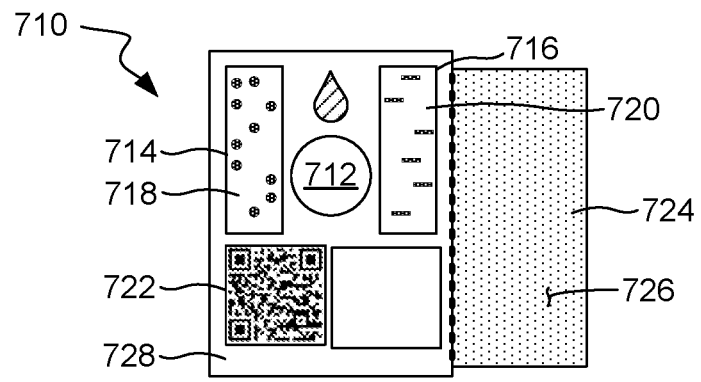
FIG. 7A depicts an exemplary lateral flow test card having a sample port, two reaction windows for viewing detection zones of dual lateral flow assays (shown at completion of test execution), and a test card QR code, along with a detachable passcode card having a scrapeable coating that conceals a passcode associated with the test card, according to one or more embodiments.
Figure 7B:
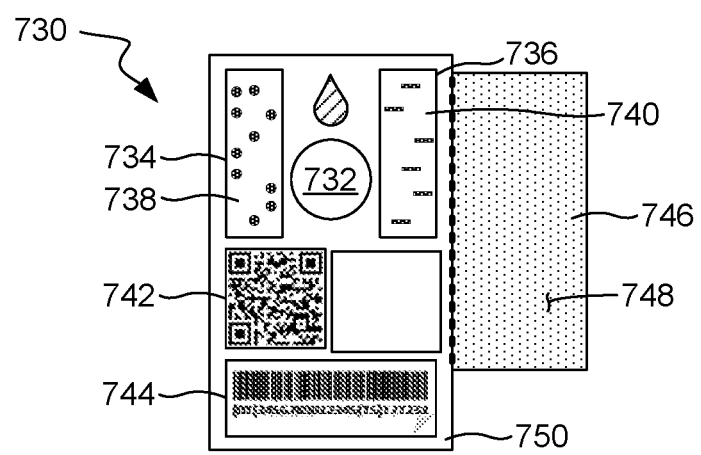
FIG. 7B depicts an exemplary lateral flow test card having a sample port, two reaction windows for viewing detection zones of dual lateral flow assays (shown at completion of test execution), a test card QR code, and a patient barcode, along with a detachable passcode card having a scrapeable coating that conceals a passcode associated with the test card, according to one or more embodiments.

The sample receiving zone 402 (e.g., a sample pad), the labeling zone 404 (e.g., a conjugate pad), the detection zone 406 (e.g., a reaction membrane), and the absorbent zone 408 (e.g., a wicking pad) are typically fixed to the substrate 410 (e.g., an inert backing material) and housed within a plastic casing with a sample port open to the sample receiving zone 402 and a reaction window showing the detection zone 406. A lateral flow assay housed in such a plastic casing is referred to herein as a "LFA test card" or "test card". FIGS. 7A and 7B show exemplary test cards in accordance some embodiments. Alternatively, in some embodiments, a lateral flow assay may be provided as a strip, in a simple dipstick format.

The sample receiving zone 402 may be provided in the form a sample pad onto which a test sample is applied. The test sample may or may not include one or more target analytes to be detected. The one or more target analytes may include, for example, one or more antigens. Some test samples (e.g., blood, serum, urine, saliva, etc.) may be placed directly onto a sample pad, while other test samples may require a dilution buffer. Still other test samples (e.g., plant material, animal feed, etc.) may require a running buffer to facilitate delivery of the test sample onto a sample pad. A sample pad may function as a filter to aid flow of the test sample and/or may be treated to adjust one or more properties (e.g., pH level, viscosity, etc.) of the test sample.

The labeling zone 404 may be provided in the form of a conjugate pad containing one or more labeling substances with antibodies that are specific for the one or more target analytes and that are conjugated to labeling particles. The labeling particles may be, for example, colloidal gold nanoparticles, latex nanoparticles, carbon nanoparticles. Colloidal gold is the most widely used labeling particle in commercial LFIAs. Other labeling particles include colored polystyrene beads. In some embodiments, the labeling zone 404 may include labeling substances with multiple colors (i.e., labeling substances that produce multiple colors upon completion of LFA test card execution). For example, labeling substances with multiple colors may be used to produce a random color pallet of test, dummy, and control patterns on the detection zone 406. Such random color pallet may be utilized, for example, to provide an additional degree of codification (e.g., the test pattern color, as well as positioning, may be randomized as the LFA test cards are manufactured) and/or to obtain information about environment light. Latex labeling particles are particularly well suited for providing such a random color pattern because latex can be produced in multiple colors.

The detection zone 406 may be provided in the form of a membrane (e.g., a nitrocellulose membrane or a cellulose acetate membrane) onto which antibodies are immobilized in lines, dots, or other patterns that define one or more test patterns, one or more dummy patterns, and one or more control patterns. In each test pattern, antibodies specific for the one or more target analytes are immobilized in a line, dot, or other pattern that crosses at least a portion of the membrane to form a test line, dot, or other pattern. In each dummy pattern, antibodies specific for the one or more non-target analytes are immobilized in a line, dot, or other pattern that crosses at least a portion of the membrane to form a dummy line, dot, or other pattern. In each control pattern, antibodies specific for the conjugate antibodies of the one or more labeling substances are immobilized in a line, dot, or other pattern that crosses at least a portion of the membrane to form a control line, dot, or other pattern.

In the embodiment illustrated in FIG. 4, the detection zone 406 includes a single test pattern 412 (e.g., a full test line, as illustrated in FIG. 4) for detecting the presence of a target analyte and a single control pattern 416 (e.g., a full control line, as illustrated in FIG. 4) for indicating the proper functioning and/or completion of an assay test. Further, in the embodiment illustrated in FIG. 4, the detection zone 406 also includes five dummy patterns 426 (e.g., five full dummy lines, as illustrated in FIG. 4) for visual obfuscation of the LFA results. To visually encode LFA results, at manufacture, one or more lines/dots containing true results of the LFA each have a position mixed with other lines/dots (i.e., "dummy" lines/dots), in randomized position patterns selected from among a plurality of possible position patterns. For example, in the exemplary lateral flow assay 400 illustrated in FIG. 4, the test point positioning of the test pattern 412 may be interchanged at manufacture with any one of the dummy pattern 426.

In accordance with one or more embodiments, the intensity of the pattern formed in the test pattern 412 after test execution may vary depending on the quantity of the target analyte present in the test sample. In accordance with one or more embodiments, the intensity of the pattern formed in the test pattern 412 after test execution is quantified to determine the concentration of the target analyte in the test sample.

The inclusion of a single test pattern 412 within the detection zone 406 as illustrated in FIG. 4 is exemplary, as is its positioning and full line configuration. One skilled in the art will appreciate that the detection zone 406 may include any number of test patterns (i.e., as long as there is at least one test pattern), at any suitable positioning and/or with any suitable configuration.

In embodiments where a detection zone includes a plurality of test patterns, the plurality of test patterns may respectively detect the presence of the same or different target analytes. Lateral flow assays having multiple test patterns that respectively detect different target analytes are referred to as "multiplexed assays". For example, in some embodiments, a first test pattern may detect the presence of a first target analyte (e.g., a target analyte related to the Dengue virus) while the second test pattern may detect the presence of a second target analyte (e.g., a target analyte related to the Zika virus). Conversely, in some embodiments, the first test pattern and the second test pattern may detect the presence of the same target analyte. For example, enhanced precision and robustness might be obtained by detecting the presence of the same target analyte using different methods and/or reagents at different test patterns.

The inclusion of a single control pattern 416 within the detection zone 406 as illustrated in FIG. 4 is exemplary, as is its positioning and full line configuration. One skilled in the art will appreciate that the detection zone 406 may include any number of control patterns (i.e., as long as there is at least one control pattern), at any suitable positioning and/or with any suitable configuration.

The inclusion of five dummy patterns 426 within the detection zone 406 as illustrated in FIG. 4 is exemplary, as is their positioning and full line configuration. One skilled in the art will appreciate that the detection zone 406 may include any number of dummy patterns (i.e., zero, one, or more), at any suitable positioning and/or with any suitable configuration.

The absorbent zone 408 may be provided in the form of a wicking pad that draws the test sample by capillary action from the sample receiving zone 402 and across the labeling zone 404 and the detection zone 406 and collects the drawn portion of the test sample.

Referring now to FIGS. 5A and 5B, an exemplary implementation of the lateral flow assay 400 shown in FIG. 4 is illustrated in accordance with one or more embodiments. In FIG. 5A, the exemplary implementation is illustrated at initiation of test execution as a test sample is applied to the sample receiving zone 402 of the lateral flow assay 400. In FIG. 5B, the exemplary implementation is illustrated at completion of test execution after the test sample has flowed across the lateral flow assay 400 to the absorbent zone 408. A test sample 502 (e.g., blood, urine, saliva, etc.) is applied to the sample receiving zone 402. In the example shown in FIGS. 5A and 5B, the test sample 502 includes a target analyte 504 (i.e., a molecule, compound, or other substance that can be assayed by the lateral flow assay 400) and a non-target analyte 506 (i.e., a molecule, compound, or other substance that is not a target analyte but is likely to be present in the test sample 502). For example, the non-target analyte 506 may be a non-specific protein always present in the test sample 502. In the illustrated embodiment, capillary action draws the test sample 502 downstream into the labeling zone 404, which contains a labeling substance 510 for indirect labeling of both the target analyte 504 and the non-target analyte 506. In the illustrated example, the labeling substance 510 may consist of an immunoglobulin 512 with a labeling particle 514 (e.g., a colloidal gold or silver particle). The immunoglobulin 512 specifically binds both the target analyte 504 and the non-target analyte 506 to form a labeled target analyte complex and a labeled non-target analyte complex, respectively. In some other implementations, the labeling substance 510 is a non-immunoglobulin labeled compound that specifically binds both the target analyte 504 and the non-target analyte 506 to form a labeled target analyte complex and a labeled non-target analyte complex, respectively.

In some other implementations, indirect labeling of the target analyte 504 and the non-target analyte 506 may be respectively provided by different labeling substances. That is, two or more labeling substances may be used in lieu of using a single labeling substance 510 that specifically binds to both the target analyte 504 and the non-target analyte 506. For example, the labeling zone 402 may contain first and second labeling substances, wherein the first labeling substance specifically binds to the target analyte 504 for indirect labeling of the target analyte 504 and the second labeling substance specifically binds to the non-target analyte 506 for indirect labeling of the non-target analyte 506.

The labeled target analyte complexes, the labeled non-target analyte complexes, along with excess quantities of the labeling substance 510, are carried along the lateral flow assay 400 into the test pattern 412, which contains immobilized compounds 520 that are capable of specifically binding the target analyte 504, and into the dummy patterns 426, which each contain immobilized compounds 522 that are capable of specifically binding to the non-target analyte 506. For the sake of clarity, only the immobilized compounds 522 contained on a single one of the five dummy patterns 426 are illustrated in FIGS. 5A and 5B. In the illustrated example, the immobilized compounds 520 may be immunoglobulins that specifically bind the labeled target analyte complexes and thereby retain the labeled target analyte complexes in the test pattern 412. Also, in the illustrated example, the immobilized compounds 522 may be immunoglobulins that specifically bind the labeled non-target analyte complexes and thereby retain the labeled non-target analyte complexes in the dummy patterns 426. The presence of the target analyte 504 in the test sample 502 typically is evidenced by a visually detectable coloring of the test pattern 412 that appears as a result of the accumulation of the labeling substance 510 in the test pattern 412. Similarly, the presence of the non-target analyte 506 in the test sample 502 is evidenced by a visually detectable coloring of the dummy patterns 426 that appears as a result of the accumulation of the labeling substance 510 in the dummy patterns 426. In some embodiments, the resulting coloring in the test pattern 412 may be similar to the resulting coloring in the dummy patterns 426. Similarity between the test pattern 412 and the dummy patterns 426, in combination with randomization of the position of the test pattern 412 at manufacture, may serve to obfuscate the LFA results evidenced in the test pattern 412.

The control pattern 416 typically is designed to indicate that an assay is functioning properly and/or has been performed to completion. Immobilized compounds 524 in the control pattern 416 bind and retain the labeling substance 510. For example, the control pattern 416 may contains anti-immunoglobulin antibodies specific for the antibody of the labeling substance 510. The labeling substance 510 typically becomes visible on the control pattern 416 after a sufficient quantity of the labeling substance 510 has accumulated. When the target analyte 504 is not present in the test sample 502, the test pattern 412 will not be colored and/or when the non-target analyte 506 is not present in the test sample 502, the dummy patterns 426 will not be colored, whereas the control pattern 416 will be colored to indicate the assay has been performed. The absorbent zone 408 captures excess quantities of the test sample 502.

Lateral flow assays may be categorized into two distinguishable formats: competitive-type assays lateral flow assays and non-competitive-type lateral flow assays. Non-competitive-type lateral flow assays are also referred to as "sandwich-format assays".

In non-competitive-type lateral flow assays, such as the lateral flow assay 400 shown in FIGS. 5A and 5B, a positive test result is represented by the presence of a colored pattern (e.g., test line, dot, or other pattern) at the test pattern and an increase in the concentration of the target analyte in the test sample results in an increase in the concentration of the labeled target analyte complex in the test pattern. For example, in the lateral flow assay 400, a positive test result is represented by the presence of a colored test line at the test pattern 412 and an increase in the concentration of the target analyte 504 in the test sample 502 results in an increase in the concentration of the labeled target analyte complex in the test pattern 412. Non-competitive-type lateral flow assays are typically used for larger target analytes, as well as target analytes with at least two binding sites, or epitopes. Also, in a non-competitive-type lateral flow assay, a colored pattern (e.g., control line, dot, or other pattern) is visible at the control pattern 416 and at the dummy patterns 426 independently of the test result. For example, at the control pattern 416, the labeling substance 510 binds to the immobilized compounds 524 (e.g., anti-immunoglobulin antibodies specific for the antibody of the labeling substance 510 immobilized at the control pattern 416). At the dummy patterns 426, labeled non-target analyte complexes bind to the immobilized compounds 522 (e.g., immunoglobulins that specifically bind the labeled non-target analyte complexes immobilized at the dummy patterns 426).

Conversely, in competitive-type lateral flow assays, a positive test result is represented by the absence of a colored pattern (e.g., test line, dot, or other pattern) at the test pattern and an increase in the concentration of the target analyte in the test sample results in a decrease in the concentration of the labeling substance in the test pattern. Competitive-type lateral flow assays are typically used for small target analytes that cannot bind to two antibodies simultaneously, as well as target analytes with only a single binding site, or epitope. In competitive-type lateral flow assays, the labeling zone may contain a labeling substance (e.g., antibody-nanoparticle conjugate) and the test pattern may contain an analyte molecule (e.g., protein-analyte complex). If the target analyte is present in the test sample, the target analyte will bind to the labeling substance and prevent the labeling substance from binding to the analyte at the test pattern. Conversely, if the target analyte is not present in the test sample, the labeling substance will bind to the analyte at the test pattern. Also, in a competitive-type lateral flow assay, a colored pattern (e.g., control line, dot, or other pattern) is visible at the control pattern and at the dummy patterns independently of the test result. For example, at the control pattern, the labeling substance binds to immobilized compounds (e.g., anti-immunoglobulin antibodies specific for the antibody of the labeling substance immobilized at the control pattern). At the dummy patterns, labeled non-target analyte complexes bind to immobilized compounds (e.g., immunoglobulins that specifically bind the labeled non-target analyte complexes immobilized at the dummy patterns).

Both competitive-type lateral flow assays and non-competitive-type lateral flow assays may be implemented as a "multiplexed assay".

Referring now to FIGS. 6A-6D, several exemplary test matrices provided on a detection zone of a lateral flow assay are depicted. The exemplary test matrices depicted in FIGS. 6A-6D are provided by a plurality of capture regions defining patterns (i.e., lines, partial lines, and dots) arranged on the detection zone of the lateral flow assay. In accordance with one or more embodiments, any one of the patterns shown in FIGS. 6A-6D may be a test pattern, a control pattern, or a dummy pattern.

In some embodiments, the test matrices may be comprised of patterns having the same color. In other embodiments, the test matrices may be comprised of patterns with multiple colors. For example, labeling substances with multiple colors may be used to produce a random color pallet of test, dummy, and control patterns on the detection zone. Such a random color pallet may be utilized, for example, to provide an additional degree of codification (e.g., the test pattern color, as well as positioning, may be randomized as the LFA test cards are manufactured) and/or to obtain information about environment light.

Figure 6A:
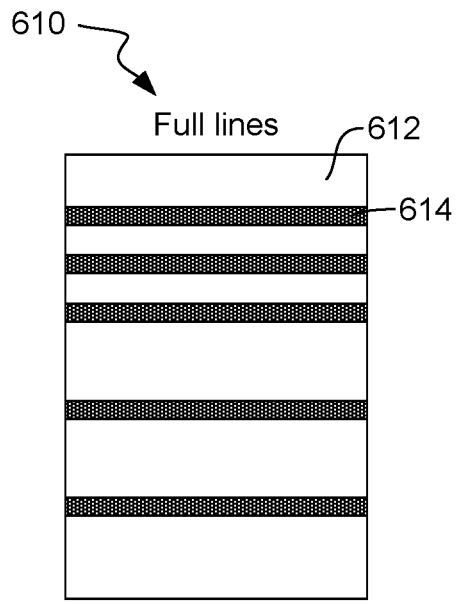
FIG. 6A depicts an exemplary test matrix on a detection zone of a lateral flow assay at completion of test execution with patterns in the form of full lines, any of which may be a test line, a control line, or a dummy line, according to one or more embodiments.

In FIG. 6A, an exemplary test matrix 610 on a detection zone 612 of a lateral flow assay is depicted at completion of test execution with patterns in the form of full lines 614 (i.e., extending fully across the detection zone 612). In accordance with one or more embodiments, any one of the full lines 614 may be a test line, a control line, or a dummy line.

Figure 6B:
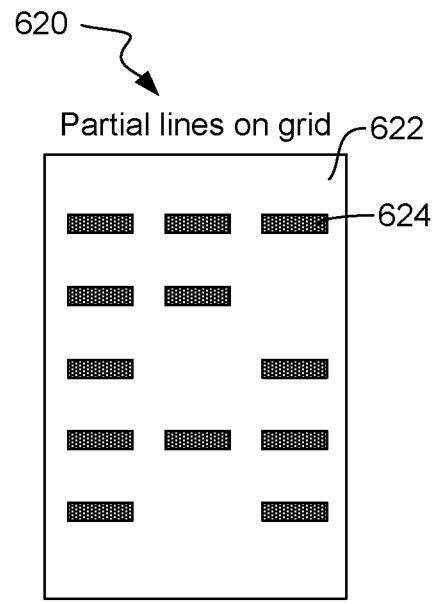
FIG. 6B depicts an exemplary test matrix on a detection zone of a lateral flow assay at completion of test execution with patterns in the form of on-grid partial lines, any of which may be a test line, a control line, or a dummy line, according to one or more embodiments.

In FIG. 6B, an exemplary test matrix 620 on a detection zone 622 of a lateral flow assay is depicted at completion of test execution with patterns in the form of partial lines 624 (i.e., extending partially across the detection zone 622) on a grid. In accordance with one or more embodiments, any of the partial lines 624 may be a test line, a control line, or a dummy line.

Figure 6C:
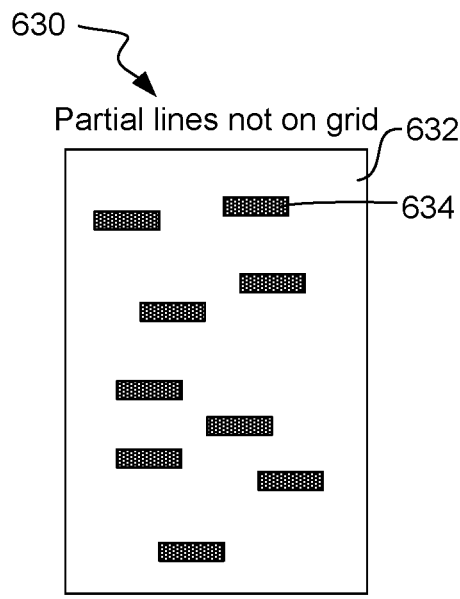
FIG. 6C depicts an exemplary test matrix on a detection zone of a lateral flow assay at completion of test execution with patterns in the form of not-on-grid partial lines, any of which may be a test line, a control line, or a dummy line, according to one or more embodiments.

In FIG. 6C, an exemplary test matrix 630 on a detection zone 632 of a lateral flow assay is depicted at completion of test execution with patterns in the form of partial lines 634 (i.e., extending partially across the detection zone 632) not on a grid. In accordance with one or more embodiments, any of the partial lines 634 may be a test line, a control line, or a dummy line.

Figure 6D:
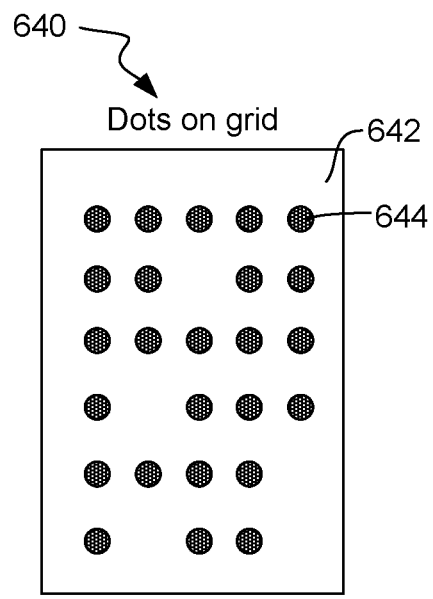
FIG. 6D depicts an exemplary test matrix on a detection zone of a lateral flow assay at completion of test execution with patterns in the form of on-grid dots, any of which may be a test dot, a control dot, or a dummy dot, according to one or more embodiments.

In FIG. 6D, an exemplary test matrix 640 on a detection zone 642 of a lateral flow assay is depicted at completion of test execution with patterns in the form of dots 644 on a grid. In accordance with one or more embodiments, any of the dots may be a test dot, a control dot, or a dummy dot.

Several commercially available reagent dispensers for producing pixelated lateral flow assays are capable of creating precise test matrices of lines or dots with suitable volumes (e.g., ranging from picoliter to nanoliter) on cellulose membranes (or other membrane materials used for the detection zone). Examples of suitable reagent dispensers include, but are not limited to, ClaremontBio's Automated Lateral Flow Reagent Dispenser (ALFRD) (available from Claremont BioSolutions, LLC, Upland, Calif.) and Matrix™ 1600 Reagent Dispensing Module (available from Kinematic Automation Inc., Twain Harte, Calif.).

Referring now to FIGS. 7A and 7B, several exemplary lateral flow test cards are depicted in accordance with some embodiments. Even though two lateral flow assays are depicted in each of the exemplary test cards depicted in FIGS. 7A and 7B, it must be understood that there may be embodiments with only one or more than two lateral flow assays in the same casing, while keeping the same described functionalities.

In FIG. 7A, an exemplary test card 710 is depicted having a sample port 712 for receiving a test sample, two reaction windows 714, 716 for viewing detection zones 718, 720 (shown at completion of test execution) of dual lateral flow assays, and a test card QR code 722, along with a detachable passcode card 724 having a scrapeable coating 726 that conceals a passcode associated with the exemplary test card 710 in accordance with one or more embodiments. The exemplary test card 710 may be fabricated of a plastic casing 728, for example, that houses the dual lateral flow assays. Alternatively, the exemplary test card 710 may be fabricated of an impermeable rigid cardboard casing or other material (in lieu of, or in addition to, the plastic casing 728). In the exemplary test card 710 illustrated in FIG. 7A, the detection zones 718, 720 have differing test matrices. For example, the detection zone 718 has patterns in form of a plurality of dots on a grid (at least one of the dots corresponds to a diagnosis and, in accordance with one or more embodiments, the location of each such diagnostic dot is randomized at fabrication). On the other hand, the detection zone 720 has patterns in the form of a plurality of partial lines on a grid (at least one of the partial lines corresponds to a diagnosis and, in accordance with one or more embodiments, the location of each such diagnostic partial line is randomized at fabrication). The test card QR code 722 may encode information specific to the exemplary test card 710, such as the test type, test card layout, test card fabrication lot, test card serial number, etc.

In FIG. 7B, an exemplary test card 730 is depicted having a sample port 732 for receiving a test sample, two reaction windows 734, 736 for viewing detection zones 738, 740 (shown at completion of test execution) of dual lateral flow assays, a test card QR code 742, and a patient barcode 744, along with a detachable passcode card 746 having a scrapeable coating 748 that conceals a passcode associated with the exemplary test card 730 in accordance with one or more embodiments. The exemplary test card 730 may be fabricated of a plastic casing 750, for example, that houses the dual lateral flow assays. Alternatively, the exemplary test card 730 may be fabricated of an impermeable rigid cardboard casing or other material (in lieu of, or in addition to, the plastic casing 750). In the exemplary test card 730 illustrated in FIG. 7B, the detection zones 738, 740 have differing test matrices. For example, the detection zone 738 has patterns in form of a plurality of dots on a grid (at least one of the dots corresponds to a diagnosis and, in accordance with one or more embodiments, the location of each such diagnostic dot is randomized at fabrication). On the other hand, the detection zone 740 has patterns in the form of a plurality of partial lines on a grid (at least one of the partial lines corresponds to a diagnosis and, in accordance with one or more embodiments, the location of each such diagnostic partial line is randomized at fabrication). The test card QR code 742 may encode information specific to the exemplary test card 730, such as the test type, test card layout, test card fabrication lot, test card serial number, etc. The patient barcode 744 may encode a patient code issued to a patient at the point-of-use. The patient code includes an ID that anonymously identifies the patient, and may also include the geolocation of the point-of-use and the time of use (e.g., the date the patient code was issued to the patient). The patient barcode 744 may be a label that is attached to the exemplary test card 730 after the patient code is issued to the patient at the point-of-use.

Figure 8:
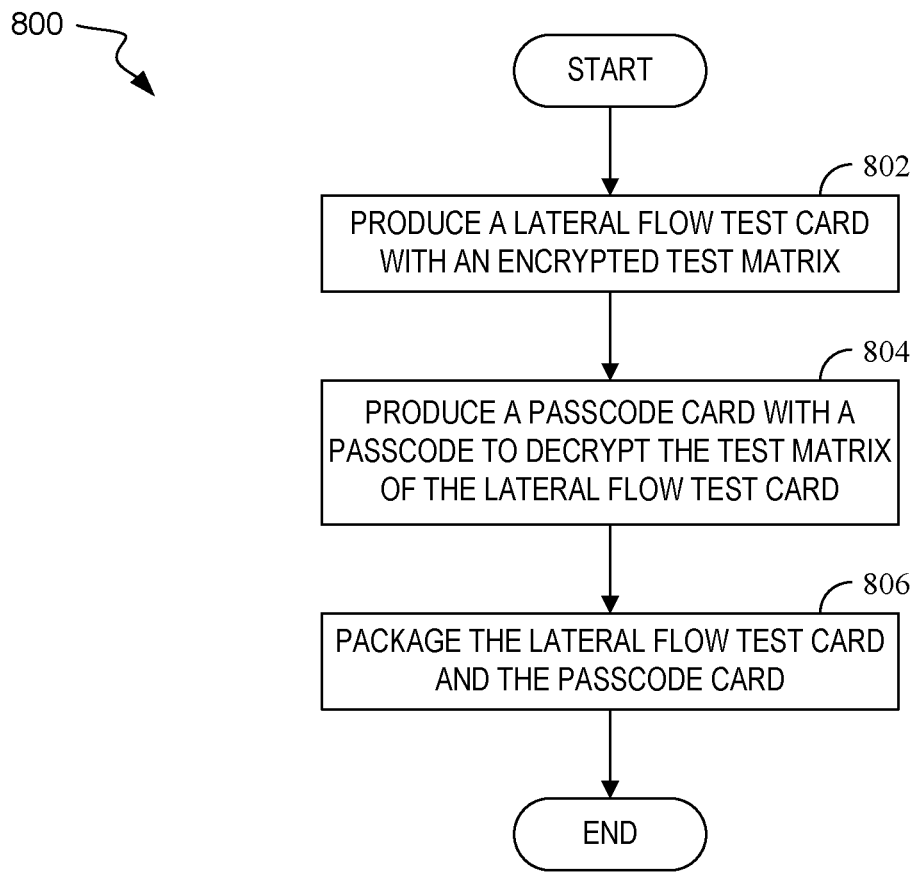
FIG. 8 is a flow diagram of an illustrative method of encrypting a lateral flow test card, according to one or more embodiments.

Referring now to FIG. 8, a flow diagram of an illustrative method 800 of encrypting a lateral flow test card is depicted in accordance with one or more embodiments. The method 800 sets forth the preferred order of the blocks. It must be understood, however, that the various blocks may occur at any time relative to one another.

Figure 9:
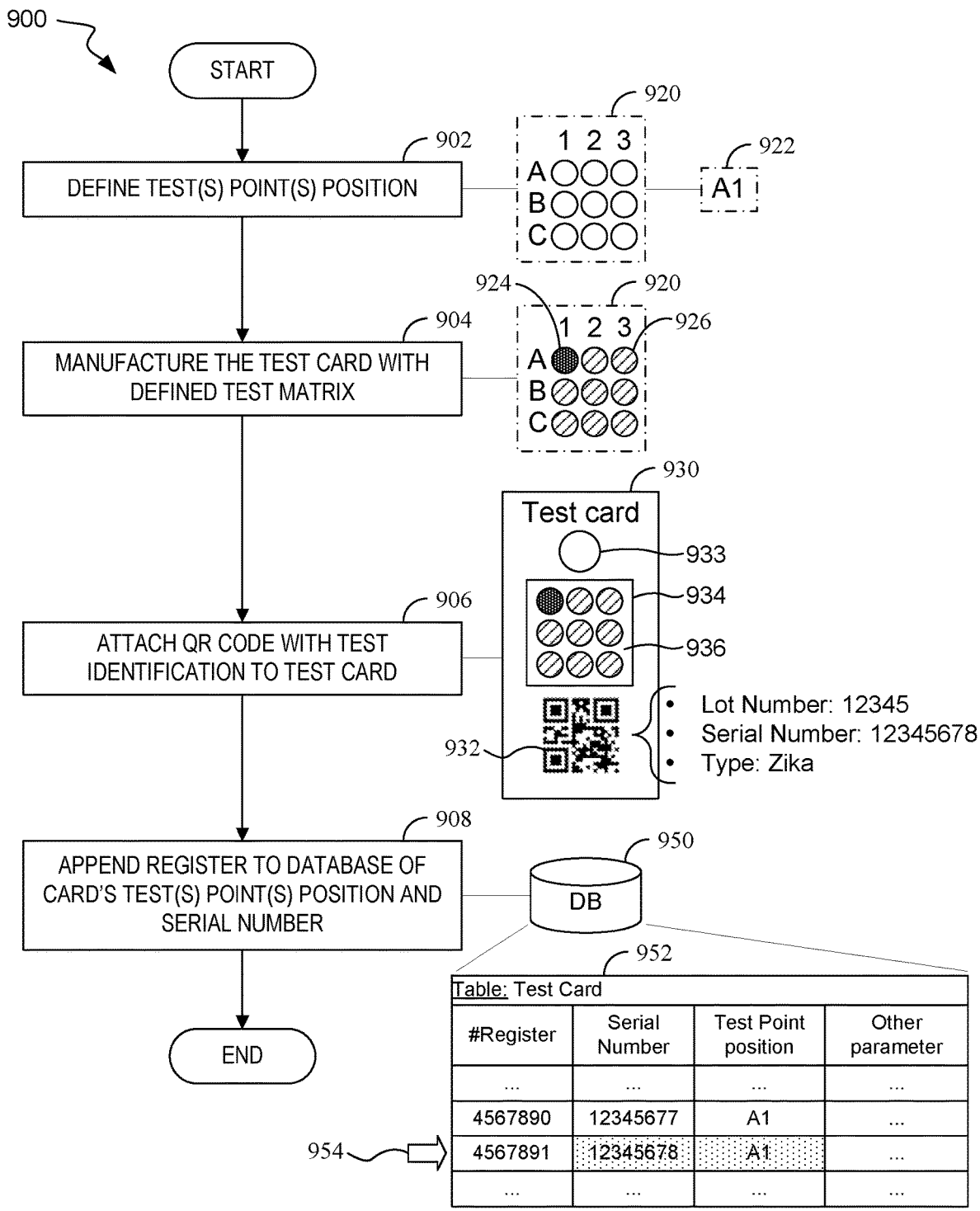
FIG. 9 is a flow diagram of an exemplary method that may be employed to encrypt a test pattern in a lateral flow test card in the illustrative method shown in FIG. 8, according to one or more embodiments.

The method 800 begins by producing a lateral flow test card with an encrypted test matrix (block 802). For example, a test card may be produced with a defined test matrix that includes one or more test patterns each dispensed at a randomized test point position within the defined test matrix. A flow diagram of an exemplary method that may be employed to produce a test card is depicted in FIG. 9, described below. The defined test matrix may encode the test results, as well as other information regarding the test and the test results.

Figure 10:
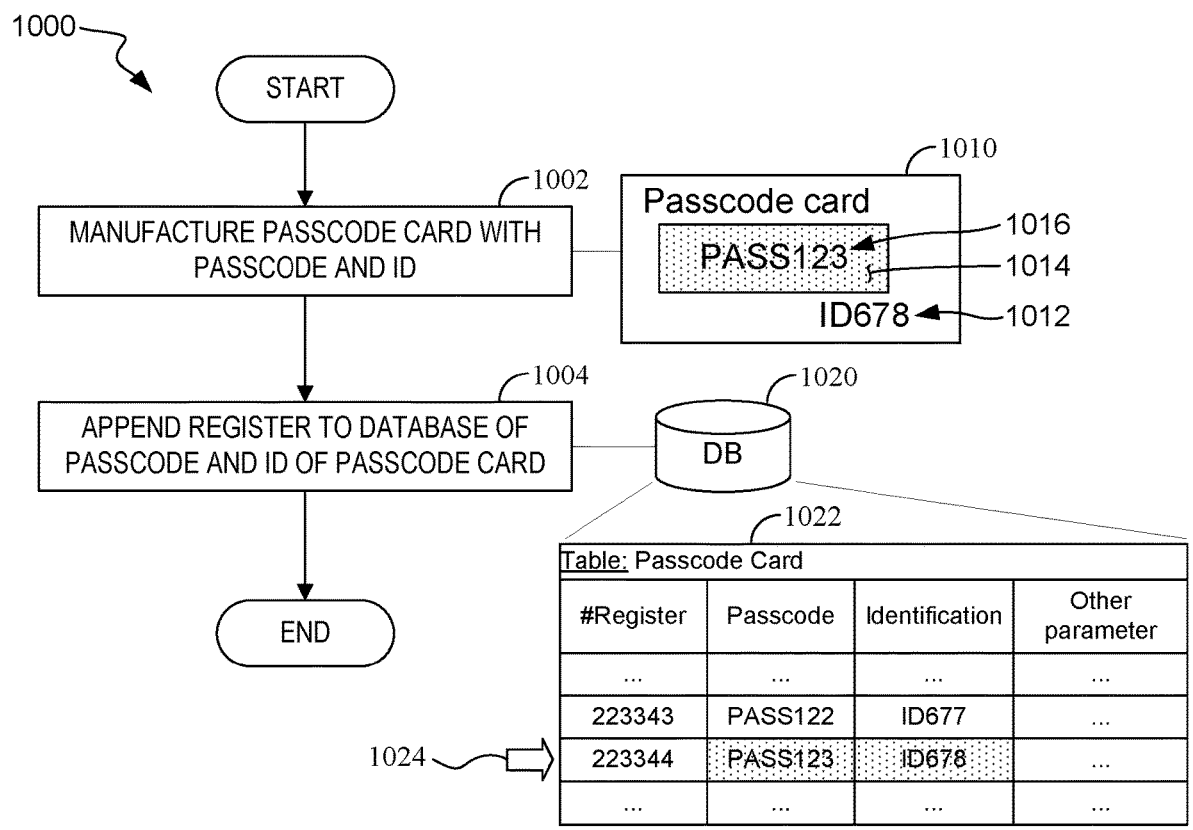
FIG. 10 is a flow diagram of an exemplary method that may be employed to define a passcode in a passcode card in the illustrative method shown in FIG. 8, according to one or more embodiments.

The method 800 continues by producing a passcode card with a passcode to decrypt the test matrix of the lateral flow test card (block 804). For example, a passcode card may be produced with a scrapeable coating that conceals a passcode that is associated with the test card produced in block 802. A flow diagram of an exemplary method that may be employed to produce a passcode card is depicted in FIG. 10, described below.

Figure 11:
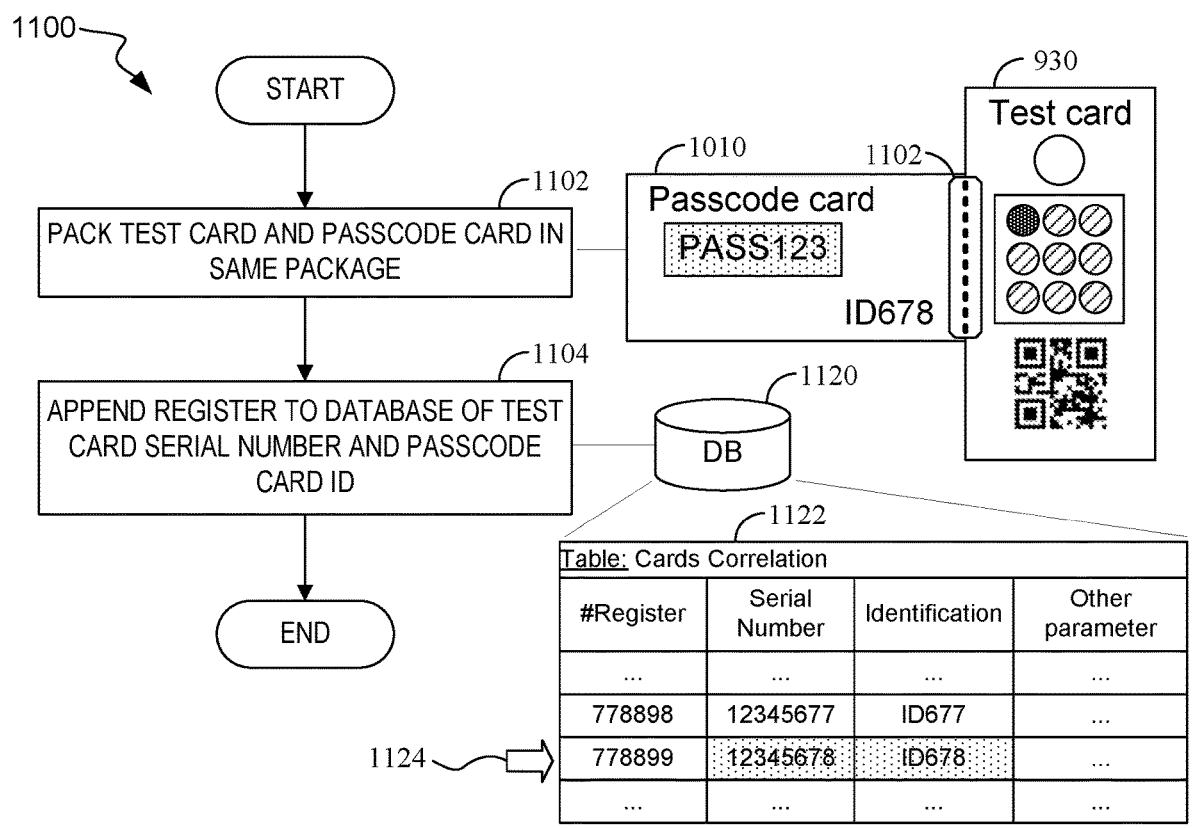
FIG. 11 is a flow diagram of an exemplary method that may be employed to package the lateral flow test card with its related passcode card in the illustrative method shown in FIG. 8, according to one or more embodiments.

The method 800 continues by packaging the lateral flow test card with its related passcode card (block 806). For example, the passcode card produced in block 804 may be attached to the test card produced in block 802 using perforated tape, in a detachable perforated sheet, originally part of the casing, or other suitable fastener that allows subsequent detachment of the passcode card from the test card. Those cards could be also produced separately and then put together in the same package (e.g., plastic bag) during the packaging process at manufacturing. A flow diagram of an exemplary method that may be employed to package the test and passcode cards is depicted in FIG. 11, described below. The method 800 may then end.

Referring now to FIG. 9, a flow diagram of an exemplary method 900 of producing a lateral flow test card is depicted in accordance with one or more embodiments. The exemplary method 900 of producing a test card depicted in FIG. 9 may correspond to block 802 in FIG. 8. The method 900 sets forth the preferred order of the blocks. It must be understood, however, that the various blocks may occur at any time relative to one another.

The method 900 begins by defining, for each test, how the test card is designed to perform, a test point position on a defined test matrix (block 902). An example defined test matrix 920 is illustrated in FIG. 9. One skilled in the art will appreciate that the example defined test matrix 920 illustrated in FIG. 9 is exemplary and non-limiting. The defined test matrix may have any configuration and any arbitrary number of dots/lines/test structures. The example defined test matrix 920 illustrated in FIG. 9 includes nine possible test point positions in the form of dots on a grid (i.e., dots at grid coordinates A1, A2, A3, B1, B2, B3, C1, C2, and C3). An example defined test point 922 is illustrated in FIG. 9, i.e., grid position A1. One skilled in the art will appreciate that the example defined test point 922 illustrated in FIG. 9 is exemplary and non-limiting. For example, in the context of the example defined test matrix 920 illustrated in the FIG. 9, the test point may be defined (i.e., randomized) at block 902 as any of the nine possible test point positons. Moreover, the test point may be redefined (i.e., randomized) at block 902 for each test card produced or for each lot of test cards produced.

The method 900 continues by manufacturing the test card with the defined test matrix (block 904). For example, in the context of the example defined test matrix 920 and the example defined test point 922 illustrated in the FIG. 9, the method 900 may use a reagent dispenser to dispense a test pattern reagent (e.g., immunoglobulins that specifically bind labeled target analyte complexes) on a reaction membrane to form a test dot 924 at grid coordinate A1 and a dummy pattern reagent (e.g., immunoglobulins that specifically bind labeled non-target analyte complexes) on the reaction membrane to form dummy dots 926 at grid coordinates A2, A3, B1, B2, B3, C1, C2, and C3. In other respects, the test card may be manufactured in block 904 using fabrication operations well known to those skilled in the art (i.e., the same fabrication operations used in the manufacture of conventional lateral flow assays).

Next, the method 900 continues by attaching a test card QR code with test identification to the test card (block 906). A portion of an example lateral flow test card 930 having an example test card QR code 932 attached thereto is illustrated in FIG. 9. The portion of the example test card 930 illustrated in FIG. 9 also includes an example sample port 933 and an example reaction window 934 for viewing an example detection zone 936 (i.e., corresponds to the example defined test matrix 920 and the example defined test point 922). One skilled in the art will appreciate that the portion of the example test card 930 illustrated in FIG. 9 is exemplary and non-limiting, as is the example test card QR code 932, the example sample port 933, the example reaction window 934, and the example detection zone 936. The test card, the test card QR code, the sample port, the reaction window, and the detection zone may have any configuration. In the example illustrated in FIG. 9, the test card QR code 932 encodes information associated with the test card, such as the test card's lot number (i.e., Lot Number: 12345), the test card's serial number (i.e., Serial Number: 12345678), and the test card's test type (i.e., Type: Zika).

The method 900 continues by appending a register to a database of the test card's serial number and, for each test, how the test card is designed to perform, the test point position (block 908). An example register 954 appended to a database 950 is illustrated in FIG. 9. One skilled in the art will appreciate that the example register 954 appended to the database 950 illustrated in FIG. 9 is exemplary and non-limiting. The register may have any configuration. The example register 954 (i.e., #Register: 4567891) illustrated in FIG. 9 is appended to a table 952 (i.e., Table: Test Card) of the database 950 and includes the test card's serial number (i.e., Serial Number: 12345678) and the test card's test point position (i.e., Test Point Position: A1), as well as any other suitable parameter(s). The method 900 may then end.

Referring now to FIG. 10, a flow diagram of an exemplary method 1000 of producing a passcode card is depicted in accordance with one or more embodiments. The exemplary method 1000 of producing a passcode card depicted in FIG. 10 may correspond to block 804 in FIG. 8. The method 1000 sets forth the preferred order of the blocks. It must be understood, however, that the various blocks may occur at any time relative to one another.

The method 1000 begins by manufacturing a passcode card with a passcode and identification (block 1002). An example passcode card 1010 having an identification 1012 (i.e., "ID678") and a scrapeable coating 1014 that conceals a passcode 1016 (i.e., "PASS123") is illustrated in FIG. 10. One skilled in the art will appreciate that the example passcode card 1010 illustrated in FIG. 10 is exemplary and non-limiting, as is the identification 1012, the scrapeable coating 1014, and the passcode 1016. The passcode card, the identification, the scrapeable coating, and the passcode may have any configuration. In accordance with some embodiments, the scrapeable coating 1014 covers at least a portion of the passcode card 1010 to conceal the passcode 1016 until the scrapeable coating 1014 is scraped away by a user to reveal the passcode 1016. In accordance with some embodiments, the passcode card 1010 may be fabricated of the same material as the test card's casing (e.g., plastic). In accordance with some embodiments, the identification 1012 and the passcode 1016 may be embossed, laser marked, or printed on a surface of the passcode card 1010. The passcode card may be manufactured in block 1002 using fabrication operations are well known to those skilled in the art (e.g., the same fabrication operations used in the manufacture of gift cards or goods packaging).

The method 1000 continues by appending a register to a database of the passcode card's passcode and identification (block 1004). An example register 1024 appended to a database 1020 is illustrated in FIG. 10. One skilled in the art will appreciate that the example register 1024 appended to the database 1020 illustrated in FIG. 10 is exemplary and non-limiting. The register may have any configuration. The example register 1024 (i.e., #Register: 223344) illustrated in FIG. 10 is appended to a table 1022 (i.e., Table: Passcode Card) of the database 1020 and includes the passcode card's passcode 1016 (i.e., Passcode: PASS123) and the passcode card's identification 1012 (i.e., Identification: ID678), as well as any other suitable parameter(s). The method 1000 may then end.

Referring now to FIG. 11, a flow diagram of an exemplary method 1100 of packaging the lateral flow test card with its related passcode card is depicted in accordance with one or more embodiments. The exemplary method 1100 of packaging test and passcode cards depicted in FIG. 11 may correspond to block 806 in FIG. 8. The method 1100 sets forth the preferred order of the blocks. It must be understood, however, that the various blocks may occur at any time relative to one another.

The method 1100 begins by packing the test card and the passcode card in the same package (block 1102). For example, the test card 930 produced according to the method 900 illustrated in FIG. 9 and the passcode card 1010 produced according to the method 1000 illustrated in FIG. 10 may be joined using perforated tape 1102, in a detachable perforated sheet, originally part of the casing, or other suitable fastener that allows subsequent detachment of the passcode card 1010 from the test card 930. The test card 930 and the passcode card 1010 could be also produced separately and then put together in the same package (e.g., plastic bag) during the packaging process at manufacturing.

The method 1100 continues by appending a register to a database of the test card's serial number and the passcode card's identification (block 1104). An example register 1124 appended to a database 1120 is illustrated in FIG. 11. One skilled in the art will appreciate that the example register 1124 appended to the database 1120 illustrated in FIG. 11 is exemplary and non-limiting. The register may have any configuration. The example register 1124 (i.e., #Register: 778899) illustrated in FIG. 11 is appended to a table 1122 (i.e., Table: Cards Correlation) of the database 1120 and includes the test card's serial number (i.e., Serial Number: 12345678) and the passcode card's identification (i.e., Identification: ID678), as well as any other suitable parameter(s). For example, the other suitable parameter(s) may include the test card's test point position and the passcode card's passcode. The method 1100 may then end.

In block 1104, the test card's serial number and the passcode card's identification may be verified optically before being appended to the database 1120 (i.e., the test card's serial number may be read indirectly using the test card's QR code and the passcode card's identification may be read directly from surface the passcode card). However, the test card's test point position (i.e., A1) and the passcode card's passcode (i.e., "PASS123") are concealed. Accordingly, in embodiments in which the test card's test point position and the passcode card's passcode are to be included among the other suitable parameter(s) of the table 1122, those parameters may be accessed from databases 950, 1020. For example, the test card's test point position may be obtained by accessing the register 954 (which was appended to the table 952 (i.e., Table: Test Card) of the database 950 in the method 900 illustrated in FIG. 9) from serial number data (i.e., 12345678). Similarly, the passcode card's passcode may be obtained by accessing the register 1024 (which was appended to the table 1022 (i.e., Table: Passcode Card) of the database 1020 in the method 1000 illustrated in FIG. 10) from identification data (i.e., ID678).

Figure 12:
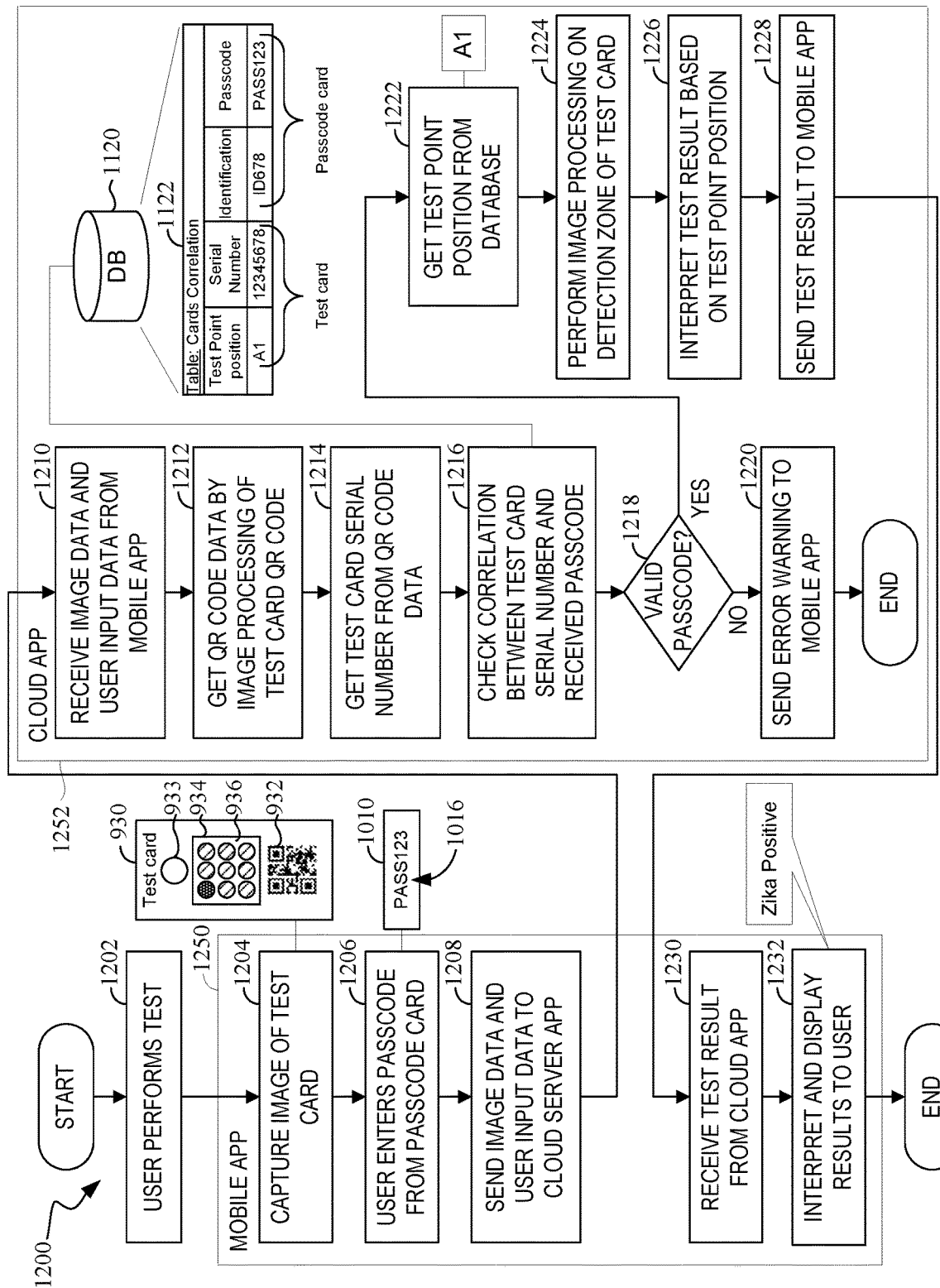
FIG. 12 is a flow diagram of an illustrative method for providing anonymized diagnosis via lateral flow assay, according to one or more embodiments.

Referring now to FIG. 12, a flow diagram of an illustrative method for providing anonymized diagnosis via lateral flow assay is depicted in accordance with one or more embodiments. The method 1200 sets forth the preferred order of the blocks. It must be understood, however, that the various blocks may occur at any time relative to one another.

In the embodiment illustrated in FIG. 12, blocks 1204, 1206, 1208, 1230, and 1232 (i.e., "mobile app" blocks denoted as 1250) may be performed at least partially by a mobile device application stored in a mobile device (e.g., the user's cellular telephone, tablet, or PDA) and blocks 1210, 1212, 1214, 1216, 1218, 1220, 1222, 1224, 1226, and 1228 (i.e., "cloud app" blocks denoted as 1252) may be performed at least partially by a cloud server application stored in one or more server devices. In one or more embodiments, the mobile device application utilized to perform blocks 1204, 1206, 1208, 1230, and 1232 may be implemented by one or more of the anonymized LFA mobile application module(s) 1334 in FIG. 13, described below. In one or more embodiments, the cloud server application utilized to perform blocks 1210, 1212, 1214, 1216, 1218, 1220, 1222, 1224, 1226, and 1228 may be implemented by one or more of the anonymized LFA cloud server application module(s) 1354 in FIG. 13, described below.

The method 1200 begins with the user performing the test (block 1202). In some embodiments, the test may be executed by a user at home. For example, the user may prick his/her finger with a sterile lancet to obtain a small sample of blood that the user may then insert in the sample port of the test card (e.g., the sample port 933 of the test card 930 produced according to the method 900 illustrated in FIG. 9). The test matrix with its random lines/dots will appear in the reaction window of the test card after the test is executed (e.g., the reaction window 934 of the test card 930 produced according to the method 900 illustrated in FIG. 9).

In block 1202, the user may be aided in performing the test by the mobile device application. For example, the mobile device application may provide the user with instructions relative to performing the test, such as how to produce a test sample, how to insert the test sample in the sample port of the test card, and an amount of time to wait after test sample insertion for the test matrix to appear in the reaction window. In some embodiments, in block 1202, the mobile device application may instruct the user to detach and secure the passcode card from the test card before performing the test. In some embodiments, the mobile device application may employ augmented reality to aid the user in performing the test.

In some embodiments, in lieu of the test being performed by the user at block 1202, the test may be executed for a user (patient) by a health care professional. For example, the test may be executed by a health care professional at a physician's office, hospital, or clinical laboratory. For example, a health care professional at a clinic may draw blood from the user (patient) into a test tube to which is attached a label with an optical machine-readable representation of data that encodes a patient code. Another health care professional at the clinic may blindly execute the test by pipetting a small sample of blood from the test tube into the sample port of the test card.

The method 1200 continues by capturing an image of the test card (block 1204). For example, the mobile device application may use a camera (e.g., the camera 1346 in FIG. 13, described below) of the mobile device to capture one or more images of a test card (e.g., the test card 930 produced according to the method 900 illustrated in FIG. 9). In the context of the test card 930, the image captured by the mobile device application using the mobile device's camera may include the test card QR code 932, the reaction window 934, and the detection zone 936. In addition, if the test card also includes a label with an optical machine-readable representation of data that encodes a patient code (e.g., the patient barcode 744 on the test card 730 illustrated in FIG. 7B), the image captured by mobile device application using the mobile device's camera may include that label as well.

In block 1204, the mobile device application may provide the user with instructions relative to capturing an image of the test card, such as where to position the mobile device relative to the test card, when the mobile device application will begin capturing an image of the test card, and when the mobile device application has successfully completed capturing an image of the test card. In some embodiments, the mobile device application may employ augmented reality to aid the user in facilitating image capture. For example, an augmented reality "digital test card image" may overlay the real image of the test card to aid the user in properly positioning the mobile device relative to the test card.

In the embodiment illustrated in FIG. 12, image processing is implemented on a cloud server application. That is, the image of the test card captured by the mobile device application using the mobile device's camera is uploaded to and analyzed by the cloud server application. In other embodiments, the mobile device application may perform at least some image processing.

The method 1200 continues with the user entering the passcode from the passcode card packaged with the test card (block 1206). For example, the mobile device application may request the user to scrape away the scrapeable coating from a passcode card (e.g., the passcode card 1010 produced according to the method 1000 illustrated in FIG. 10) to reveal a passcode and to then enter the passcode. In the context of the passcode card 1010, scraping away the scrapeable coating from the passcode card 1010 reveals the passcode 1016 (i.e., "PASS123"), which the user enters into the mobile device. In some embodiments, the mobile device application may have earlier (e.g., in block 1202) instructed the user to detach and secure the passcode card 1010 from the test card 930.

Next, the method 1200 continues with the mobile device application sending image data and user input data to the cloud server application (block 1208). For example, the mobile device application may use one or more communication components (e.g., the communication component(s) 1330 in FIG. 13, described below) of the mobile device to send to the cloud server application the image captured by the mobile device application using the mobile device's camera and the passcode 1016 (i.e., "PASS123") entered into the mobile device by the user. In some embodiments, in block 1208, the mobile device application may send additional data to the cloud server application, such as geolocation data using a global satellite-based geolocation system (e.g., the GPS 1344 in FIG. 13, described below) of the mobile device.

The method 1200 continues with the cloud server application receiving image data and user input data from the mobile device application (block 1210). For example, the cloud server application may use one or more communication components (e.g., the communication component(s) 1350 in FIG. 13, described below) of one or more servers to receive the image of the test card captured by the mobile device application and the passcode 1016 (i.e., "PASS123") entered into the mobile device by the user. In some embodiments, in block 1210, the cloud server application may receive additional data from the mobile device application, such as geolocation data.

Next, the method 1200 continues with the cloud server application getting QR code data by image processing of the test card QR code (block 1212). For example, the cloud server application may perform image processing on the received image of the test card to recognize the test card QR code 932 and obtain QR code data. The cloud server application may employ conventional, well-known image processing techniques to recognize and decode the test card QR code 932 and/or any other optical machine-readable representation of data included in the received image of the test card.

The method 1200 continues with the cloud server application getting the test card serial number from the QR code data (block 1214). For example, the cloud server application may use the QR code data obtained from the test card QR code 932 in block 1212 to decode the test card serial number (i.e., 12345678) encoded within the test card QR code 932.

Next, the method 1200 continues with the cloud server application checking correlation between the test card serial number and the received passcode (block 1216). For example, the cloud server application may check the table 1122 (i.e., Table: Cards Correlation) of the database 1120 for correlation between the decoded test card serial number (i.e., Serial Number: 12345678) and the received passcode 1016 (i.e., "PASS123").

If the test card additionally includes a label with an optical machine-readable representation of data that encodes a patient code (e.g., the patient barcode 744 on the test card 730 illustrated in FIG. 7B), the image processing performed by the cloud server application in block 1212 may recognize the label and decode the patient code as well.

The method 1200 then continues with the cloud server application determining whether the received passcode is valid (block 1218). For example, the cloud server application may determine validity by matching the received passcode 1016 (i.e., "PASS123") against the Passcode entry from the register in the table 1122 (i.e., Table: Cards Correlation) of the database 1120 corresponding to the decoded test card serial number (i.e., Serial Number: 12345678).

In response to determining the received passcode is not valid (block 1218=NO), the method 1200 continues with the cloud server application sending an error warning to the mobile device application (block 1220). For example, the error warning sent by the cloud server application to the mobile device application at block 1220 may warn the user that an error has been detected. The method 1200 may then end. In some embodiments, the error warning may request the user to re-enter the passcode from the passcode card.

In response to determining the received passcode is valid (block 1218=YES), the method 1200 continues with the cloud server application getting the test point position from one or more database (block 1222). For example, the cloud server application may access the database 1120 to retrieve the test card's test point position (i.e., Test Point position: A1) from the register in the table 1122 (i.e., Table: Cards Correlation) corresponding to the decoded test card serial number (i.e., Serial Number: 12345678). In other embodiments, the cloud server application may access one or more other databases (e.g., database 950 in FIG. 9) to retrieve the test card's test point position.

Upon retrieving the test card's test point position, the cloud server application may employ one or more image processing methods on the detection zone of the test card (block 1224) and interpret the test result based on retrieved test point position (block 1226). Any suitable image processing method(s) capable of extracting test line(s) and/or test dot(s) from the test matrix may be used to interpret the test matrix. After extracting test line(s) and/or test dot(s) from the test matrix, additional image processing steps may also be applied (e.g., obtain mean RGB/HSV color values of the diagnosis test line/test dot and use it as input for a machine learning algorithm to obtain Zika virus concentration estimative) to further obtain additional data. Three exemplary image processing methods that may be used in accordance with some embodiments of the present invention are described below.

A first exemplary image processing method delimits a "region of interest" over a readout region to remove unnecessary structures in the analysis image. For example, if the test card has dual lateral flow assays (e.g., the test card 710 in FIG. 7A and the test card 730 in FIG. 7B), the first exemplary image processing method delimits a "region of interest" over a readout region that encompasses both of the reaction windows. The region of interest may be a predefined portion of the test card (e.g., upper two-thirds) or may be encoded in the test card QR code (e.g., encoded as a component of the test card layout). The image in the region of interest is divided in half (e.g., vertically). Then, on each half, rectangles present in the region of interest are detected. On each half, the largest rectangle is the reaction window of the lateral flow assay under analysis and is used to further crop the image. In test cards having at least one lateral flow assay with patterns in the form of lines, rectangles are then detected within the reaction window of each lateral flow assay with lines. Within each such reaction window, the rectangles with largest width and height are counted as the lines of the lateral flow assay. In test cards having at least one lateral flow assay with patterns in the form of dots, circles are then detected within the reaction window of each lateral flow assay with dots. Within each such reaction window, the circles with similar sizes are counted as the dots of the lateral flow assay. The detected rectangles counted as lines and/or the detected circles counted as dots can then be used as a mask to obtain the colorimetric information of the test line or test dot at each test point position of the test card. This colorimetric information may be used for ambient light compensation (for dummy lines/dots) or for concentration estimation (for diagnosis lines/dots).

A second exemplary image processing method delimits a "region of interest" over a readout region to remove unnecessary structures in the analysis image. For example, if the test card has dual lateral flow assays (e.g., the test card 710 in FIG. 7A and the test card 730 in FIG. 7B), the second exemplary image processing method delimits a "region of interest" over a readout region that encompasses both of the reaction windows. The region of interest may be a predefined portion of the test card (e.g., upper two-thirds) or may be encoded in the test card QR code (e.g., encoded as a component of the test card layout). The image in the region of interest is converted to grayscale, to obtain lines or dots only. The greyscale image is then divided into two parts, in which each part has only one of the lateral flow assay under analysis. After division, the obtained images are further cropped to remove unwanted lines related to the reaction window. In test cards having at least one lateral flow assay with patterns in the form of lines, rectangles are then detected and each rectangle is counted as a line of the lateral flow assay. In test cards having at least one lateral flow assay with patterns in the form of dots, circles are then detected and each circle is counted as a dot of the lateral flow assay. The detected rectangles counted as lines and/or the detected circles counted as dots can then be used as a mask to obtain the colorimetric information of the test line or test dot at each test point position of the test card. This colorimetric information may be used for ambient light compensation (for dummy lines/dots) or for concentration estimation (for diagnosis lines/dots).

A third exemplary image processing method delimits a "region of interest" over a readout region to remove unnecessary structures in the analysis image. For example, if the test card has dual lateral flow assays (e.g., the test card 710 in FIG. 7A and the test card 730 in FIG. 7B), the third exemplary image processing method delimits a "region of interest" over a readout region that encompasses both of the reaction windows. The region of interest may be a predefined portion of the test card (e.g., upper two-thirds) or may be encoded in the test card QR code (e.g., encoded as a component of the test card layout). The image in the region of interest is converted to grayscale, to obtain lines or dots only. The grayscale image is then divided into a plurality of parts, in which each part has only one line or dot analysis (i.e., no more than one detected line subject to analysis or no more than one detected dot subject to analysis). After division, the obtained images are further cropped to remove unwanted lines related to the reaction window. In test cards having at least one lateral flow assay with patterns in the form of lines, if the detected line has a minimum number of pixels (e.g., 10 black pixels or more), that line is counted as a line of the lateral flow assay. In test cards having at least one lateral flow assay with patterns in the form of dots, if the detected dot has a minimum number of pixels (e.g., 7 black pixels or more), that dot is counted as a dot of the lateral flow assay. The detected lines counted as lines and/or the detected dots counted as dots can then be used as a mask to obtain the colorimetric information of the test line or test dot at each test point position of the test card. This colorimetric information may be used for ambient light compensation (for dummy lines/dots) or for concentration estimation (for diagnosis lines/dots).

Generally, as in each of the three exemplary image processing methods, detected objects counted as lines and/or dots of a lateral flow assay can be used as a mask to obtain the colorimetric information of the test line or test dot at each test point positon of the test card. For example, in a test card having a lateral flow assay with patterns in the form of dots, the mask may be used to obtain the colorimetric information of the test dot at each test point position on the lateral flow assay's detection zone. Similarly, in a test card having a lateral flow assay with patterns in the form of lines, the mask may be used to obtain the colorimetric information of the test line at each test point position on the lateral flow assay's detection zone. The mask may be used to map out the test matrix and, for each given test point position, determine which of the detected objects is the test pattern (e.g., test line or test dot). Then, the colorimetric information of each detected object that is determined to be a test pattern (e.g., test line or test dot) is obtained.

In some embodiments, the image processing method may employ calibration data that correlate the colorimetric information (e.g., color values, color intensity, etc.) detected at each test pattern (e.g., test line or test dot) and the concentration of the target analyte in the test sample. In some embodiments, the calibration data may be lot dependent (i.e., the calibration data may vary from lot to lot). In some embodiments, the image processing method may extract the test card's lot number from the test card QR code and employ calibration data tailored for the particular lot in which the test card was manufactured. For example, the cloud server application may access a calibration database (e.g., the calibration database 1322 in FIG. 13, described below) to obtain calibration data tailored for the particular lot in which the test card was manufactured.

The test result, in accordance with some embodiments, may include one or more target analyte concentration values, one or more diagnoses, and/or one or more confidence levels. The one or more target analyte concentration values of the test result may each represent the concentration of a target analyte in the test sample and may be determined based on the colorimetric information detected at respective test patterns and calibration data. In some embodiments, at least one of the target analyte concentration values may represent the average of target analyte concentration values determined using different methods and/or reagents at different test patterns. The one or more diagnoses of the test result may each represent a diagnosis associated with one or more target analytes and may be determined by comparing each determined target analyte concentration value to a threshold concentration value that represents a positive diagnosis. The one or more confidence levels of the test result may represent the level of confidence associated with each diagnosis and may be determined based on myriad factors, such as the number of pixels in detected objects counted as test patterns, statistical analysis of the accuracy of the calibration data, statistical analysis of the accuracy of past diagnoses using identically manufactured test cards, the consistency of the target analyte concentration values obtained using different methods and/or reagents at different test patterns, etc.

Next, the method 1200 continues with the cloud server application sending the test result to the mobile device application (block 1228). For example, the cloud server application may use one or more communication components (e.g., the communication component(s) 1350 in FIG. 13, described below) of one or more servers to send the test result to the mobile device application.

In some embodiments, at least part of the image processing to interpret the test card's test matrix may be performed by mobile device application. For example, in lieu of sending the test result to the mobile device application at block 1228, the cloud server application may send each test point position of the test card to the mobile device application, along with the test card's lot number. One or more image processing methods performed by the mobile device application to interpret the test card's test matrix may then employ calibration data tailored for the particular lot in which the test card was manufactured. For example, the mobile device application may access a calibration database (e.g., the calibration database 1322 in FIG. 13, described below) to obtain the calibration data tailored for the particular lot in which the test card was manufactured.

The method 1200 continues with the mobile device application receiving the test result from the cloud server application (block 1230). For example, the mobile device application may use one or more communication components (e.g., the communication component(s) 1330 in FIG. 13, described below) of the mobile device to receive the test result.

Next, the method 1200 continues with the mobile device application interpreting and displaying the test results to the user (block 1232). For example, the mobile device application may interpret the test result received from the cloud server application and, based on that interpretation of the test result, use a display (e.g., the display 1342 in FIG. 13, described below) of the mobile device to display test card results (e.g., Zika Positive). The method 1200 may then end.

Figure 13:
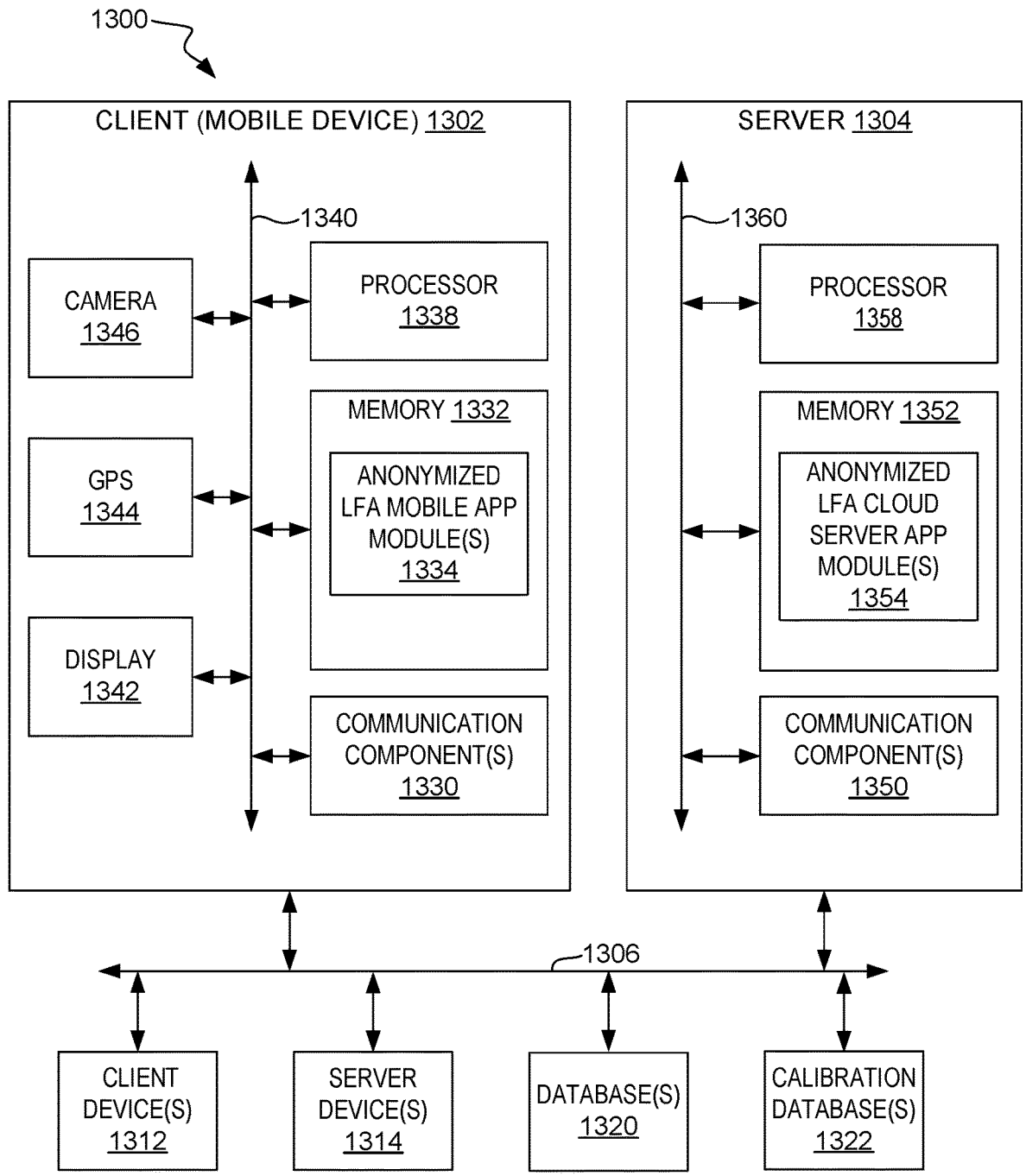
FIG. 13 illustrates a block diagram of an example, non-limiting system that facilitates anonymized diagnosis via lateral flow assay, according to one or more embodiments.

Referring now to FIG. 13, a block diagram of an example, non-limiting system 1300 that facilitates anonymized diagnosis via lateral flow assay is illustrated in accordance with one or more embodiments. Repetitive description of like elements employed in other embodiments described herein is omitted for the sake of brevity. Aspects of systems (e.g., system 1300 and the like), apparatuses, or processes explained in this disclosure may constitute machine-executable program module(s) embodied within machine(s), e.g., embodied in one or more computer readable mediums (or media) associated with one or more machines. Such program module(s), when executed by the one or more machines, e.g., one or more computers, one or more computing devices, one or more virtual machines, etc., may cause the one or more machines to perform the operations described.

As shown in FIG. 13, the system 1300 may include one or more client systems (mobile devices) 1302, 1312, one or more server systems 1304, 1314, one or more networks 1306, one or more databases 1320, and one or more calibration databases 1322. It is to be appreciated that the one or more client systems 1302, 1312, the one or more server systems 1304, 1314, the one or more databases 1320, and the one or more calibration databases 1322 may be equipped with communication devices (e.g., one or more communication components 1330, described below, with respect to the client system 1302) that enable communication between the one or more client systems 1302, 1312, the one or more server systems 1304, 1314, the one or more databases 1320, and the one or more calibration databases 1322 over the one or more networks 1306.

Client systems 1302, 1312 may include the structure and/or functionality described herein with respect to the mobile app blocks 1250 in FIG. 12 (e.g., test card image capture, passcode entry, interpretation and display of test results to user, etc.). Client system 1312 may be a different type of client system than client system 1302. Client system 1312 may also be a client system 1302 and/or include one or more components of client system 1302. It is to be appreciated that in discussions below where more than one client system is employed, the client system may include one or more client systems 1302 and/or one or more client systems 1312.

Server systems 1304, 1314 may include the functionality described herein with respect to the cloud app blocks 1252 in FIG. 12 (e.g., image processing, passcode validation, test matrix resolution, etc.). Server system 1314 may be a different type of client system than server system 1304. Server system 1314 may also be a server system 1304 and/or include one or more components of server system 1304. It is to be appreciated that in discussions below where more than one server system is employed, the server systems may include one or more server systems 1304 and/or one or more server systems 1314.

The various components (e.g., client systems 1302, 1312, server systems 1304, 1314, databases 1320, calibration databases 1322, communication components 1330, 1350, memory 1332, 1352, processor 1338, 1358, display 1342, GPS 1344, camera 1346, and/or other components) of system 1300 may be connected directly or via one or more networks 1306. Such networks 1306 may include wired and wireless networks, including, but not limited to, a cellular network, a wide area network (WAN) (e.g., the Internet), and/or a local area network (LAN), non-limiting examples of which include cellular, WAN, wireless fidelity (Wi-Fi), Wi-Mal, WLAN, radio communication, microwave communication, satellite communication, optical communication, sonic communication, electromagnetic induction communication, quantum communication, and/or any other suitable communication technology.

Client system 1302 may include one or more communication components 1330 that enable client system 1302 to communicate with one or more server systems 1304, 1314, one or more other client devices 1312, one or more databases 1320, and/or one or more calibration databases 1322 over one or more networks 1306 via wireless and/or wired communications. For example, the one or more communication components 1330 may correspond to network adapter 20 in FIG. 1.

Client system 1302 may include or otherwise be associated with at least one memory 1332 that may store computer executable program module(s) (e.g., computer executable program module(s) may include, but are not limited to, anonymized LFA mobile app module(s) 1334 and associated program module(s)). Anonymized LFA mobile app module(s) 1334 may correspond to program modules 42 in FIG. 1, as well as the mobile app blocks 1250 in FIG. 12. Client system 1302 may also include or otherwise be associated with at least one processor 1338 that executes the computer executable program module(s) stored in the memory 1332. Client system 1302 may further include a system bus 1340 that may couple the various components including, but not limited to, communication component(s) 1330, memory 1332, processor 1338, display 1342, GPS 1344, camera 1346, and/or other components (e.g., accelerometer, gyroscope, magnetometer).

While the client system 1302 is shown in FIG. 13 as including anonymized LFA mobile app module(s) 1334, in other embodiments, any number of different types of devices may be associated with or include all or some of the anonymized LFA mobile app module(s) 1334. For example, one or more server systems 1304, 1314 may include all or some of the anonymized LFA mobile app module(s) 1334. In other words, data processing associated with the mobile app blocks 1250 in FIG. 12 (e.g., test card image capture, passcode entry, interpretation and display of test results to user, etc.) may be performed locally (e.g., using the processor 1338) and/or remotely (e.g., at server system 1304 using processor 1358). All such embodiments are envisaged.

Client system 1302 may also include or otherwise be associated with at least one display 1342 that may display test results, as well as information related to using the test card and anonymized LFA mobile app module(s) 1334. The display 1342 may be any suitable display device. For example, the display 1342 may be a display that is integrated into a mobile phone, tablet, PDA, or laptop. In other embodiments, the display 1342 may be a component of a device (e.g., test card reader) communicatively coupled to a mobile phone, tablet, PDA, or laptop. Additionally, the display 1342 may also be attached to the mobile device 1302 via communication component(s) 1330, via wired and/or wireless communication methods.

Client system 1302 may also include or otherwise be associated with at least one GPS 1344 that may provide geolocation data. The GPS 1344 may be any suitable global satellite-based geolocation system, such as the Global Positioning System (GPS), GLObal Navigation Satellite System (GLONASS), Galileo, Quasi-Zenith Satellite System (QZSS), etc. For example, the GPS 1344 may be a global satellite-based geolocation system that is integrated into a mobile phone, tablet, PDA, or laptop. In other embodiments, the GPS 1344 may be a component of a device (e.g., test card reader) communicatively coupled to a mobile phone, tablet, PDA, or laptop. Additionally, the GPS 1344 may also be attached to the mobile device 1302 via communication component(s) 1330, via wired and/or wireless communication methods.

Client system 1302 may also include or otherwise be associated with at least one camera 1346 that may capture an image of one or more portions of the test card. The camera 1346 may be any suitable image capture device. For example, the camera 1346 may be a camera that is integrated into a mobile phone, tablet, PDA, or laptop. In other embodiments, the camera 1346 may be a component of a device (e.g., a test card reader) communicatively coupled to a mobile phone, tablet, PDA, or laptop.

Server system 1304 may include one or more communication components 1350 that enable server system 1304 to communicate with one or more client systems 1302, 1312, one or more other server devices 1314, one or more databases 1320, and/or one or more calibration databases 1322 over one or more networks 1306 via wireless and/or wired communications. For example, the one or more communication components 1350 may correspond to network adapter 20 in FIG. 1.

Server system 1304 may include or otherwise be associated with at least one memory 1352 that may store computer executable program module(s) (e.g., computer executable program module(s) may include, but are not limited to, anonymized LFA cloud server app module(s) 1354 and associated program module(s)). Anonymized LFA cloud server app module(s) 1354 may correspond to program modules 42 in FIG. 1, as well as the cloud app blocks 1252 in FIG. 12. Server system 1304 may also include or otherwise be associated with at least one processor 1358 that executes the computer executable program module(s) stored in the memory 1352. Server system 1304 may further include a system bus 1360 that may couple the various components including, but not limited to, communication component(s) 1350, memory 1352, processor 1358, and/or other components.

While the server system 1304 is shown in FIG. 13 as including anonymized LFA cloud server app module(s) 1354, in other embodiments, any number of different types of devices may be associated with or include all or some of the anonymized LFA cloud server app module(s) 1354. For example, one or more client systems 1302, 1312 may include all or some of the anonymized LFA cloud server app module(s) 1354. In other words, data processing associated with the cloud app blocks 1252 in FIG. 12 (e.g., image processing, passcode validation, test matrix resolution, etc.) may be performed locally (e.g., using the processor 1358) and/or remotely (e.g., at client system 1302 using processor 1338). All such embodiments are envisaged.

The one or more databases 1320 may be any database, non-limiting examples of which include one or more databases that store test card data from test card manufacture (e.g., the database 950 in FIG. 9), one or more databases that store passcode card data from passcode card manufacture (e.g., the database 1020 in FIG. 10), and one or more databases that store card correlation data from packaging together test cards and passcode cards (e.g., the database 1120 in FIGS. 11 and 12).

The one or more calibration databases 1322 may be one or more test card calibration databases, non-limiting examples include one or more test card calibration databases that store calibration data that correlate colorimetric information (e.g., color values, color intensity, etc.) detected at each test pattern (e.g., test line or test dot) of a test card and concentration of the target analyte in the test sample.

Even though a new lot of test cards utilizes the same chemical analysis as a previous lot of test cards, implementation of a lot-based calibration procedure may be necessary, due to variations in the manufacturing process from lot to lot. Accordingly, in some embodiments, the one or more calibration databases 1322 may the store calibration data on a lot-by-lot basis, i.e., the calibration data may be tailored for each lot of test cards manufactured. For example, the calibration data may be obtained by executing a calibration procedure, for each lot of test cards manufactured, by pipetting standard solutions (i.e., each standard solution having a known concentration of each target substance) on a representative number of test cards from each lot and then, once an appropriate amount of time has passed, capturing an image of each test card's test matrix and performing image processing on the image to correlate the concentration values of the target substances and color values detected on each test pattern.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In one or more embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects are described herein with reference to flowchart illustrations and/or block diagrams of methods, apparatus (systems), and computer program products according to one or more embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

One skilled in the art will appreciate that many variations are possible within the scope of the present invention. For example, the particular hardware and software implementation details described herein are merely for illustrative purposes and are not meant to limit the scope of the described subject matter. Thus, while the present invention has been particularly shown and described with reference to preferred embodiments thereof, it will be understood by those skilled in the art that changes in form and details may be made therein without departing from the spirit and scope of the present invention.

What is claimed is:

1. A method for anonymized diagnosis, the method comprising:
   receiving, at a server device, image data and user input data including a passcode from a mobile device, wherein the image data is based on an image of one or more portions of a test card, wherein the test card comprises:
      one or more lateral flow assay on a membrane having a test matrix comprising one or more test patterns, one or more dummy patterns, and one or more control patterns, wherein a test point position of each test pattern in the test matrix is randomized at manufacture; and
      an optical machine-readable representation of data that encodes optically verifiable test card identification information associated with the test card;
   in response to the receiving, determining, at the server device, whether the passcode included in the user input data received from the mobile device is valid by checking a database for correlation between the encoded optically verifiable test card identification information and the passcode;
   in response to determining that the passcode is valid, at the server device, retrieving a register associated with a serial number of the test card, wherein the register defines, for the test matrix, the test point position of each test pattern;
   determining, based on the test point position from the register, a location of each test pattern in the image data;
   interpreting the image data at the determined location of each test pattern to determine a test result of the lateral assay; and
   sending, at the server device, the test result to the mobile device.

2. The method as recited in claim 1, further comprising:
   capturing, at the mobile device, the image of the one or more portions of the test card;
   receiving, at the mobile device, the user input data; and
   sending, at the mobile device, the image data and the user input data to the server device for analysis.

3. The method as recited in claim 2, further comprising:
receiving, at the mobile device, the test result from the server device;
interpreting, at the mobile device, the test result received from the server device; and
displaying, at the mobile device, test card results based on the interpreting operation.

* * * * *